US012648753B2

(12) United States Patent
Cohen et al.

(10) Patent No.: US 12,648,753 B2
(45) Date of Patent: Jun. 9, 2026

(54) CONTROL OF LASER ATHERECTOMY BY CO-REGISTERED INTRAVASCULAR IMAGING

(71) Applicant: PHILIPS IMAGE GUIDED THERAPY CORPORATION, San Diego, CA (US)

(72) Inventors: Asher Cohen, San Diego, CA (US); Pei-Yin Chao, Eindhoven (NL)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 90 days.

(21) Appl. No.: 18/082,458

(22) Filed: Dec. 15, 2022

(65) Prior Publication Data

US 2023/0190229 A1     Jun. 22, 2023

Related U.S. Application Data

(60) Provisional application No. 63/290,706, filed on Dec. 17, 2021.

(51) Int. Cl.
*A61B 8/12*        (2006.01)
*A61B 8/08*        (2006.01)
*A61B 6/00*        (2006.01)

(52) U.S. Cl.
CPC .............. *A61B 8/12* (2013.01); *A61B 8/0891* (2013.01); *A61B 6/5247* (2013.01)

(58) Field of Classification Search
None
See application file for complete search history.

(56) References Cited

U.S. PATENT DOCUMENTS

| | | | |
|---|---|---|---|
| 4,887,605 | A | 12/1989 | Angelsen |
| 6,200,268 | B1 | 3/2001 | Vince |
| 6,381,350 | B1 | 4/2002 | Klingensmith |
| 6,776,763 | B2 | 8/2004 | Nix |
| 7,074,188 | B2 | 7/2006 | Nair |
| 7,175,597 | B2 | 2/2007 | Vince |

(Continued)

FOREIGN PATENT DOCUMENTS

| | | |
|---|---|---|
| WO | 2022078744 A1 | 4/2022 |
| WO | 2022238092 A1 | 11/2022 |

*Primary Examiner* — Katherine L Fernandez

(57) ABSTRACT

A system includes a processor circuit in communication with an intraluminal imaging device and a laser atherectomy device. An intraluminal imaging procedure is performed within a lumen with the intraluminal imaging device. The processor circuit receives the intraluminal images acquired. The intraluminal images are analyzed to determine a tissue classification for each intraluminal image. One or more laser atherectomy settings are determined for each intraluminal image based on the tissue classification. The intraluminal images and corresponding tissue classifications and laser atherectomy settings are then associated with the location at which each intraluminal image was acquired along the lumen. A laser atherectomy procedure is then performed within the same lumen. As the laser atherectomy device is moved to positions within the vessel, the laser atherectomy setting associated with each position is retrieved from the memory and automatically applied to the laser atherectomy device.

12 Claims, 17 Drawing Sheets

(56)                    References Cited

U.S. PATENT DOCUMENTS

| | | | |
|---|---|---|---|
| 7,215,802 B2 | 5/2007 | Klingensmith | |
| 7,226,417 B1 | 6/2007 | Eberle | |
| 7,359,554 B2 | 4/2008 | Klingensmith | |
| 7,463,759 B2 | 12/2008 | Klingensmith | |
| 7,846,101 B2 | 12/2010 | Eberle | |
| 7,846,191 B2 | 12/2010 | Vaynberg | |
| 7,930,014 B2 | 4/2011 | Huennekens | |
| 7,941,000 B2 | 5/2011 | Rongen | |
| 8,290,228 B2 | 10/2012 | Cohen | |
| 8,463,007 B2 | 6/2013 | Steinberg | |
| 8,670,603 B2 | 3/2014 | Tolkowsky | |
| 8,693,756 B2 | 4/2014 | Tolkowsky | |
| 8,781,193 B2 | 7/2014 | Steinberg | |
| 8,855,744 B2 | 10/2014 | Tolkowsky | |
| 9,931,171 B1* | 4/2018 | Peyman | A61B 3/14 |
| 10,076,301 B2 | 9/2018 | Millett | |
| 11,413,017 B2 | 8/2022 | Stigall | |
| 2005/0251116 A1 | 11/2005 | Steinke | |
| 2010/0042084 A1 | 2/2010 | Nariyuki | |
| 2010/0114094 A1* | 5/2010 | Thapliyal | G16H 50/50 600/463 |
| 2014/0180273 A1* | 6/2014 | Nair | A61B 18/1492 606/34 |
| 2016/0184021 A1 | 6/2016 | Kowalewski | |
| 2016/0317119 A1* | 11/2016 | Tahmasebi Maraghoosh | A61B 8/085 |
| 2018/0221100 A1* | 8/2018 | Berry | A61B 18/14 |
| 2019/0282182 A1 | 9/2019 | Scott | |
| 2019/0282211 A1 | 9/2019 | Merritt | |
| 2020/0029861 A1 | 1/2020 | Rajguru | |
| 2020/0029932 A1 | 1/2020 | Cohen | |
| 2020/0397312 A1* | 12/2020 | Ben Oren | G16H 40/63 |

* cited by examiner

| Tissue Type | Extent | Status | Fluence | Rate |
|---|---|---|---|---|
| Calcium | ##.# mm², ##.#% | | | |
| Fibrous | ##.# mm², ##.#% | | | |
| Necrotic Core | ##.# mm², ##.#% | On | ## mJ/mm2 | ## pulses/sec |
| Fibro-Fatty | ##.# mm², ##.#% | | | |
| ... | ... | | | |

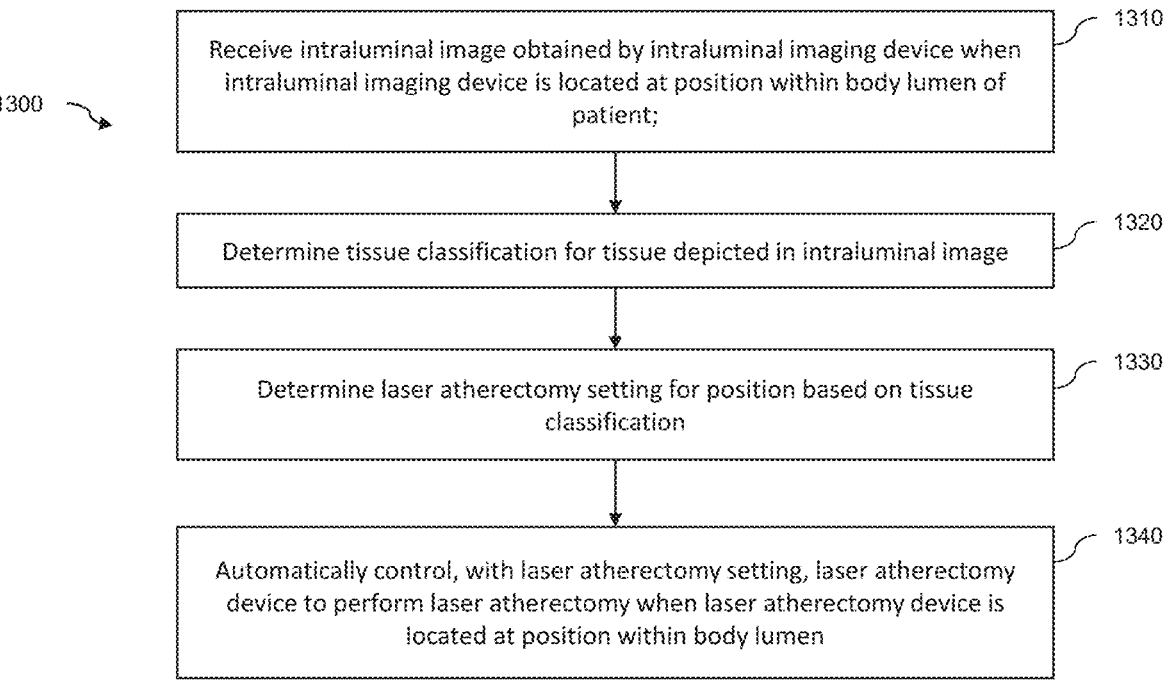

1300

1310 — Receive intraluminal image obtained by intraluminal imaging device when intraluminal imaging device is located at position within body lumen of patient;

1320 — Determine tissue classification for tissue depicted in intraluminal image 1330 — Determine laser atherectomy setting for position based on tissue classification 1340 — Automatically control, with laser atherectomy setting, laser atherectomy device to perform laser atherectomy when laser atherectomy device is located at position within body lumen

Fig. 13

CONTROL OF LASER ATHERECTOMY BY CO-REGISTERED INTRAVASCULAR IMAGING

CROSS-REFERENCE TO RELATED APPLICATIONS

This application claims priority to and the benefit of U.S. Provisional Application No. 63/290,706, filed Dec. 17, 2021, which is incorporated by reference herein in its entirety.

TECHNICAL FIELD

The present disclosure relates generally to configuring laser atherectomy settings for an atherectomy procedure. In particular, laser atherectomy settings are automatically adjusted as an atherectomy device moves through a vessel. The laser atherectomy settings are based on intravascular data coregistered to locations along the vessel.

BACKGROUND

Physicians use many different medical diagnostic systems and tools to monitor a patient's health and diagnose and treat medical conditions. Different modalities of medical diagnostic systems may provide a physician with different images, models, and/or data relating to internal structures within a patient. These modalities include invasive devices and systems, such as intravascular systems, and non-invasive devices and systems, such as x-ray systems, and computed tomography (CT) systems. In addition, different medical treatment systems for different procedures provide a physician with different options to remedy observed medical conditions of patients. Using multiple diagnostic systems in combination with treatment systems to examine and remedy a patient's medical condition provides a physician with added insight into the condition of the patient, as well as additional tools and guidance during a treatment procedure.

In the field of intravascular imaging and physiology measurement, co-registration of data from invasive devices (e.g., intravascular ultrasound (IVUS) devices or instantaneous wave-free ratio (iFR) devices) with images collected non-invasively (e.g., via x-ray angiography) is a powerful technique for improving the efficiency and accuracy of vascular catheterization procedures. Co-registration identifies the locations of intravascular data measurements along a blood vessel by mapping the data to an angiography image of the vessel. A physician may then know exactly where in the vessel a measurement was made, rather than estimate the location.

In the field of intravascular treatment, physicians use many devices to remedy conditions of decreased blood flow in patients. A laser atherectomy device is used by a physician to clear away obstructions within a blood vessel with a laser to restore blood flow. Laser based coronary atherectomy is commonly used for patients with in-stent restenosis, stent under expansion, balloon uncrossable lesions and chronic total occlusions. The overall goal of atherectomy can be to enable easier stent delivery, increased stent expansion, and avoidance of issues such as no reflow or distal embolization. Some treatment systems provide physicians with guidance related to a treatment procedure as well as views of the patient anatomy. During a laser atherectomy procedure, a physician is required to constantly adjust the settings of the device laser based on the size and type of obstruction to be cleared. For example, a region of a vessel with large amounts of hard calcium deposits may require a higher intensity laser setting. By contrast, regions of little to no obstruction material or soft tissue may require a lower intensity laser setting to prevent perforations, dissections, or other unnecessary damage to the blood vessel from the laser. Requiring a physician to manually adjust laser settings during a procedure presents a greater risk of error leading to further complications. Today, laser atherectomy is an important but a time consuming and delicate trial and error step in the completion of complex percutaneous coronary intervention (PCI) procedures.

SUMMARY

Embodiments of the present disclosure are systems, devices, and methods for automatically adjusting laser atherectomy settings based on intravascular data coregistered to locations along a blood vessel. The settings of a laser atherectomy device determine the intensity of the laser used to clear obstructions from inside a blood vessel. These settings must be adjusted depending on the type of obstruction. The disclosed systems, devices, and methods advantageously assist a physician by adjusting the settings of a laser atherectomy device so the intensity of the laser is appropriate for each location along the blood vessel. This advantageously ensures that the laser atherectomy device uses a high intensity laser for regions of hard deposits and uses a low intensity laser for regions of soft deposits. In this way, trauma to the surrounding vessel may be minimized while maximizing the efficacy of a laser atherectomy procedure. Aspects of the present disclosure also advantageously lower procedure time of a laser atherectomy procedure.

At a first step, an intravascular ultrasound (IVUS) pullback procedure may be performed. During an IVUS pullback procedure, an IVUS imaging device is positioned within a blood vessel and acquires IVUS images showing the interior of a blood vessel as it moves through the vessel. The IVUS device may pass through regions with no obstructions to blood flow or regions with substantial obstructions to blood flow, as well as anything in between. A processor circuit of the system may analyze each IVUS image to determine how much and what type of material or tissue is shown in each image. The processor circuit may then recommend laser atherectomy settings, including a fluence setting and a rate setting, for each IVUS image. As an example, an IVUS image with large regions of hard material, such as calcium deposits, may be assigned a high fluence setting and a high rate setting. However, an IVUS image showing no obstructive material may be assigned a setting to turn off the laser atherectomy device for that region.

During the IVUS imaging procedure, the location of the IVUS imaging device may be tracked in multiple x-ray images. By coregistration of a pathway of movement of the IVUS device to a view of the blood vessel in an x-ray image, the IVUS images received, as well as the laser atherectomy device settings for each IVUS image, may be associated with a location along the vessel.

After the IVUS pullback procedure is complete, a laser atherectomy device is positioned within the vessel. As the atherectomy device moves to each location along the vessel, the laser settings associated with each location may be applied. In this way, the laser atherectomy device applies the recommended settings to each region of the vessel to effectively clear away regions of hard plaque with higher intensity settings when needed and ensuring lower intensity settings are used for other regions.

According to an exemplary aspect, a system is provided. The system includes a processor circuit configured for communication with an intraluminal imaging device and a laser atherectomy device, wherein the processor circuit is configured to: receive an intraluminal image obtained by the intraluminal imaging device when the intraluminal imaging device is located at a position within a body lumen of a patient; determine a tissue classification for tissue depicted in the intraluminal image; determine a laser atherectomy setting for the position based on the tissue classification; and automatically control, with the laser atherectomy setting, the laser atherectomy device to perform laser atherectomy when the laser atherectomy device is located at the position within the body lumen.

In some aspects, the processor circuit is configured to: receive a plurality of intraluminal images obtained by the intraluminal imaging device when the intraluminal imaging device is located at a plurality of positions within the body lumen during movement of the intraluminal imaging device through the body lumen; determine a plurality of tissue classifications for the tissue depicted in the plurality of intraluminal images; determine a plurality of laser atherectomy settings for the plurality of positions; and automatically control, with the plurality of laser atherectomy settings, laser atherectomy device to perform the laser atherectomy during movement of the laser atherectomy device through the body lumen. In some aspects, the processor circuit is configured to: receive a further intraluminal obtained by the intraluminal imaging device when the intraluminal imaging device is positioned at a further position within the body lumen during movement of the intraluminal imaging device through the body lumen; determine a further tissue classifications for the tissue depicted in the further intraluminal image; determine a further laser atherectomy setting for the further position; automatically change from the laser atherectomy setting to the further laser atherectomy setting when the laser atherectomy device moves from the position to the further position. In some aspects, the processor circuit is configured to: co-register the tissue classification with the position; determine if the laser atherectomy device is located at the position; and automatically apply the laser atherectomy setting to the laser atherectomy device in response to the determination that the laser atherectomy device is located at the position. In some aspects, the processor circuit is configured to determine the laser atherectomy setting for the position in response to the determination that the laser atherectomy device is located at the position. In some aspects, the processor circuit is configured to: determine the laser atherectomy setting for the position in response to the determination of the tissue classification; co-register the laser atherectomy setting with the position; determine if the laser atherectomy device is located at the position; and automatically apply the laser atherectomy setting to the laser atherectomy device in response to the determination that the laser atherectomy device is located at the position. In some aspects, the laser atherectomy setting comprises a fluence setting. In some aspects, the laser atherectomy setting comprises a rate setting. In some aspects, the laser atherectomy setting comprises an on/off setting. In some aspects, to determine the tissue classification for the tissue, the processor circuit is configured to identify a region depicted in the intraluminal image with a type of tissue. In some aspects, the type of tissue comprises calcium. In some aspects, the processor circuit is further configured to output, to one or more displays in communication with the processor circuit, one or more screen displays comprising the laser atherectomy setting. In some aspects, the processor circuit is further configured to output, to a display in communication with the processor circuit, a screen display comprises: the laser atherectomy setting; and at least one of the intraluminal image, an extraluminal image depicting the body lumen, or a longitudinal view of the body lumen generated based on a plurality of intraluminal images.

According to an exemplary aspect, a method is provided. The method includes receiving, using a processor circuit in communication with an intraluminal imaging device, an intraluminal image obtained by the intraluminal imaging device when the intraluminal imaging device is located at a position within a body lumen of a patient; determining, using the processor circuit, a tissue classification for tissue depicted in the intraluminal image; determine, using the processor circuit, a laser atherectomy setting for the position based on the tissue classification; and automatically control, using the processor circuit, the laser atherectomy device with the laser atherectomy setting to perform laser atherectomy when the laser atherectomy device is located at the position within the body lumen.

According to an exemplary aspect, a system is provided. The system includes a processor circuit configured for communication with an intravascular imaging device, an x-ray imaging device, and a laser atherectomy device, wherein the processor circuit is configured to: receive a first plurality of x-ray images obtained by the x-ray imaging device during movement of the intravascular imaging device within a blood vessel of a patient, wherein the first plurality of x-ray images show a radiopaque portion of the intravascular imaging device; receive a plurality of intravascular images obtained by the intravascular imaging device during the movement of the intravascular imaging device; determine a plurality of tissue classifications for the plurality of IVUS images; determine a plurality of laser atherectomy settings based on the plurality of tissue classification; associate the plurality of laser atherectomy settings with corresponding positions along the blood vessel; receive a second plurality of x-ray images obtained by the x-ray imaging device during movement of the laser atherectomy device within the blood vessel, wherein the second plurality of x-ray images show a radiopaque portion of the laser atherectomy device; as the laser atherectomy device is positioned at each position of the corresponding positions: apply a laser atherectomy setting of the plurality of laser atherectomy settings associated with the position of the laser atherectomy device; output, to a screen display in communication with processor circuit, a screen display comprising: an intravascular image of the plurality of intravascular images associated with the position of the laser atherectomy device; the laser atherectomy setting; and an x-ray image of the second plurality of x-ray images showing the radiopaque portion of the laser atherectomy device.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 13 is a flow diagram of a method of automatically adjusting laser atherectomy settings based on coregistration of intraluminal data and extraluminal data, according to aspects of the present disclosure.

DETAILED DESCRIPTION

Figure 1A:
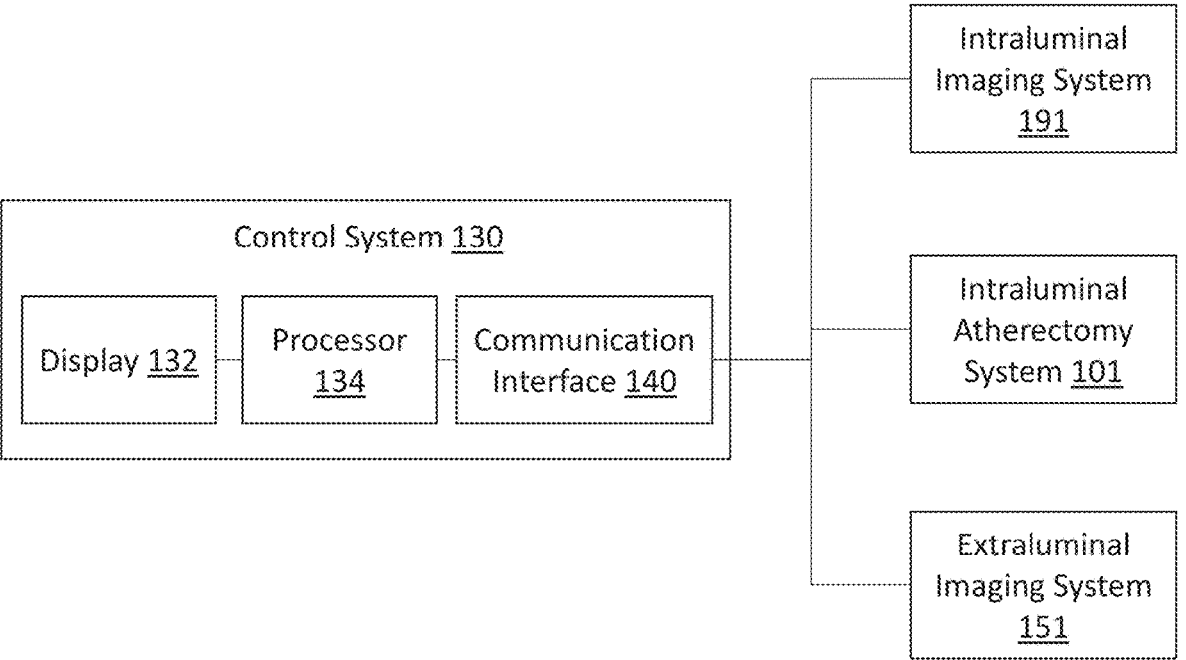
FIG. 1A is a schematic diagram of an intraluminal atherectomy, extraluminal imaging, and intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1A is a schematic diagram of an intraluminal atherectomy, extraluminal imaging, and intraluminal imaging system 100, according to aspects of the present disclosure. In some embodiments, the intraluminal atherectomy system, extraluminal imaging system, and the intraluminal imaging system, may be three separate systems or may be a combination of three systems: an intraluminal atherectomy system 101, an extraluminal imaging system 151, and an intraluminal imaging system 191. The intraluminal atherectomy system 101 may be configured to remove or soften blockages within a blood vessel. For example, the intraluminal atherectomy system 101 can control an intraluminal device to remove unwanted regions of tissue or plaque build-up within a blood vessel inside the patient's body. The extraluminal imaging system 151 obtains medical data about the patient's body while the extraluminal imaging device 152 is positioned outside the patient's body. For example, the extraluminal imaging system 151 can control extraluminal imaging device 152 to obtain extraluminal images of the inside of the patient's body while the extraluminal imaging device 152 is outside the patient's body. The intraluminal imaging system 191 also obtains medical data about a patient's body, but while an intraluminal device is positioned inside the patient's body. For example, the intraluminal imaging system 101 can control an intraluminal device to obtain intraluminal data of the inside of the patient's body while the intraluminal device is inside the patient's body.

The intraluminal atherectomy system 101 may be in communication with the extraluminal imaging system 151 through any suitable components. Such communication may be established through a wired cable, through a wireless signal, or by any other means. In addition, the intraluminal atherectomy system 101 may be in continuous communication with the x-ray system 151 or may be in intermittent communication. For example, the two systems may be brought into temporary communication via a wired cable, or brought into communication via a wireless communication, or through any other suitable means at some point before, after, or during an examination. In addition, the intraluminal atherectomy system 101 may receive data such as x-ray images, annotated x-ray images, metrics calculated with the extraluminal imaging system 151, information regarding dates and times of examinations, types and/or severity of patient conditions or diagnoses, patient history or other patient information, or any suitable data or information from the x-ray imaging system 151. The x-ray imaging system 151 may also receive various data from the intraluminal atherectomy system 101. In some embodiments, and as shown in FIG. 1A, the intraluminal atherectomy system 101 and the x-ray imaging system 151 may be in communication with the same control system 130. In this embodiment, both systems may be in communication with the same display 132, processor 134, and communication interface 140 shown as well as in communication with any other components implemented within the control system 130. In some embodiments, the intraluminal atherectomy system 101 may be in communication with a separate control system and the extraluminal imaging system 151 may in communication with a different control system.

The intraluminal imaging system 191 may be in communication with the extraluminal imaging system 151 through any suitable components. Such communication may be established through a wired cable, through a wireless signal, or by any other means. In addition, the intraluminal imaging system 191 may be in continuous communication with the x-ray system 151 or may be in intermittent communication. For example, the two systems may be brought into temporary communication via a wired cable, or brought into communication via a wireless communication, or through any other suitable means at some point before, after, or during an examination. In addition, the intraluminal imaging system 191 may receive data such as x-ray images, annotated x-ray images, metrics calculated with the x-ray imaging system 151, information regarding dates and times of examinations, types and/or severity of patient conditions or diagnoses, patient history or other patient information, or any suitable data or information from the x-ray imaging system 151. The x-ray imaging system 151 may also receive various data from the intraluminal imaging system 191. In some embodiments, and as shown in FIG. 1A, the intraluminal imaging system 191 and the x-ray imaging system 151 may be in communication with the same control system 130. In this embodiment, both systems may be in communication with the same display 132, processor 134, and communication interface 140 shown as well as in communication with any other components implemented within the control system 130. In some embodiments, the intraluminal imaging system 191 may be in communication with a separate control system and the extraluminal imaging system 151 may in communication with a different control system.

The intraluminal imaging system 191 may also be in communication with the intraluminal atherectomy system 101 through any suitable components. Such communication may be established through a wired cable, through a wireless signal, or by any other means. In addition, the intraluminal imaging system 191 may be in continuous communication with the intraluminal atherectomy system 101 or may be in intermittent communication. For example, the two systems may be brought into temporary communication via a wired cable, or brought into communication via a wireless communication, or through any other suitable means at some point before, after, or during an examination. In addition, the intraluminal imaging system 191 may receive data such as pressure data, blood flow data, metrics calculated with the intraluminal atherectomy system 101, information regarding dates and times of examinations, types and/or severity of patient conditions or diagnoses, device settings for procedures or locations along a vessel, patient history or other patient information, or any suitable data or information from the intraluminal atherectomy system 101. The intraluminal atherectomy system 101 may also receive various data from the intraluminal imaging system 191. In some embodiments, and as shown in FIG. 1A, the intraluminal imaging system 191 and the intraluminal atherectomy system 101 may be in communication with the same control system 130. In this embodiment, both systems may be in communication with the same display 132, processor 134, and communication interface 140 shown as well as in communication with any other components implemented within the control system 130. In some embodiments, the intraluminal imaging system 191 may be in communication with a separate control system and the intraluminal atherectomy system 101 may in communication with a different control system.

In some embodiments, the system 100 may not include a control system 130 in communication with the physiology measurement system 101, the intraluminal imaging system 191, and/or the x-ray imaging system 151. Instead, the system 100 may include separate control systems. For example, one control system may be in communication with or be a part of the intraluminal atherectomy system 101, one control system may be in communication with or be a part of the intraluminal imaging system 191, and an additional separate control system may be in communication with or be a part of the x-ray imaging system 151. In this embodiment, the separate control systems of the intraluminal atherectomy system 101, the intraluminal imaging system 191, and the x-ray imaging system 151 may be similar to the control system 130. For example, each control system may include various components or systems such as a communication interface, processor, and/or a display. In this embodiment, any of the control systems of the intraluminal atherectomy system 101, the intraluminal imaging system 191, or the extraluminal imaging system 151 may perform any or all of the coregistration steps described in the present disclosure. In some embodiments, one control system may be in communication with, and may be configured to control, both the intraluminal imaging system 191 and the intraluminal atherectomy system 101, while a separate control system controls the extraluminal imaging system 151. In other embodiments, one control system may be in communication with, and may be configured to control, the intraluminal imaging system 191 and the extraluminal imaging system 151, while a separate control system controls the intraluminal atherectomy system 101. In other embodiments, one control system may be in communication with, and may be configured to control, the intraluminal atherectomy system 101 and the extraluminal imaging system 151, while a separate control system controls the intraluminal imaging system 191.

Figure 1B:
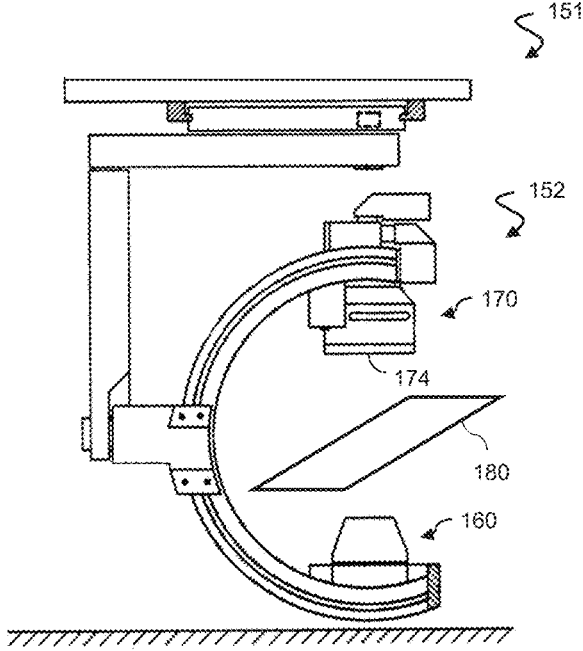
FIG. 1B is a diagrammatic view of an extraluminal imaging system, according to aspects of the present disclosure.

FIG. 1B is a diagrammatic view of an extraluminal imaging system 151, according to aspects of the present disclosure. The extraluminal imaging system or x-ray imaging system 151 may include an x-ray imaging apparatus or device 152 configured to perform x-ray imaging, angiography, fluoroscopy, radiography, venography, among other imaging techniques. The x-ray imaging system 151 can generate a single x-ray image (e.g., an angiogram or venogram) or multiple (e.g., two or more) x-ray images (e.g., a video and/or fluoroscopic image stream) based on x-ray image data collected by the x-ray device 152. The x-ray imaging device 152 may be of any suitable type, for example, it may be a stationary x-ray system such as a fixed c-arm x-ray device, a mobile c-arm x-ray device, a straight arm x-ray device, or a u-arm device. The x-ray imaging device 152 may additionally be any suitable mobile device. The x-ray imaging device 152 may also be in communication with the control system 130. In some embodiments, the x-ray system 151 may include a digital radiography device or any other suitable device.

The x-ray device 152 as shown in FIG. 1 includes an x-ray source 160 and an x-ray detector 170 including an input screen 174. The x-ray source 160 and the detector 170 may be mounted at a mutual distance. Positioned between the x-ray source 160 and the x-ray detector 170 may be an anatomy of a patient or object 180. For example, the anatomy of the patient (including the vessel 120) can be positioned between the x-ray source 160 and the x-ray detector 170.

The x-ray source 160 may include an x-ray tube adapted to generate x-rays. Some aspects of the x-ray source 160 may include one or more vacuum tubes including a cathode in connection with a negative lead of a high-voltage power source and an anode in connection with a positive lead of the same power source. The cathode of the x-ray source 160 may additionally include a filament. The filament may be of any suitable type or constructed of any suitable material, including tungsten or rhenium tungsten, and may be positioned within a recessed region of the cathode. One function of the cathode may be to expel electrons from the high voltage power source and focus them into a well-defined beam aimed at the anode. The anode may also be constructed of any suitable material and may be configured to create x-radiation from the emitted electrons of the cathode. In addition, the anode may dissipate heat created in the process of generating x-radiation. The anode may be shaped as a beveled disk and, in some embodiments, may be rotated via an electric motor. The cathode and anode of the x-ray source 160 may be housed in an airtight enclosure, sometimes referred to as an envelope.

In some embodiments, the x-ray source 160 may include a radiation object focus which influences the visibility of an image. The radiation object focus may be selected by a user of the system 100 or by a manufacture of the system 100 based on characteristics such as blurring, visibility, heat-dissipating capacity, or other characteristics. In some embodiments, an operator or user of the system 100 may switch between different provided radiation object foci in a point-of-care setting.

The detector 170 may be configured to acquire x-ray images and may include the input screen 174. The input screen 174 may include one or more intensifying screens configured to absorb x-ray energy and convert the energy to light. The light may in turn expose a film. The input screen 174 may be used to convert x-ray energy to light in embodiments in which the film may be more sensitive to light than x-radiation. Different types of intensifying screens within the image intensifier may be selected depending on the region of a patient to be imaged, requirements for image detail and/or patient exposure, or any other factors. Intensifying screens may be constructed of any suitable materials, including barium lead sulfate, barium strontium sulfate, barium fluorochloride, yttrium oxysulfide, or any other suitable material. The input screen 374 may be a fluorescent screen or a film positioned directly adjacent to a fluorescent screen. In some embodiments, the input screen 374 may also include a protective screen to shield circuitry or components within the detector 370 from the surrounding environment. In some embodiments, the x-ray detector 170 may include a flat panel detector (FPD). The detector 170 may be an indirect conversion FPD or a direct conversion FPD. The detector 170 may also include charge-coupled devices (CCDs). The x-ray detector 370 may additionally be referred to as an x-ray sensor.

The object 180 may be any suitable object to be imaged. In an exemplary embodiment, the object may be the anatomy of a patient. More specifically, the anatomy to be imaged may include chest, abdomen, the pelvic region, neck, legs, head, feet, a region with cardiac vasculature, or a region containing the peripheral vasculature of a patient and may include various anatomical structures such as, but not limited to, organs, tissue, blood vessels and blood, gases, or any other anatomical structures or objects. In other embodiments, the object may be or include man-made structures.

In some embodiments, the x-ray imaging system 151 may be configured to obtain x-ray images without contrast. In some embodiments, the x-ray imaging system 151 may be configured to obtain x-ray images with contrast (e.g., angiogram or venogram). In such embodiments, a contrast agent or x-ray dye may be introduced to a patient's anatomy before imaging. The contrast agent may also be referred to as a radiocontrast agent, contrast material, contrast dye, or contrast media. The contrast dye may be of any suitable material, chemical, or compound and may be a liquid, powder, paste, tablet, or of any other suitable form. For example, the contrast dye may be iodine-based compounds, barium sulfate compounds, gadolinium-based compounds, or any other suitable compounds. The contrast agent may be used to enhance the visibility of internal fluids or structures within a patient's anatomy. The contrast agent may absorb external x-rays, resulting in decreased exposure on the x-ray detector 170.

In some embodiments, the extraluminal imaging system 151 could be any suitable extraluminal imaging device, such as computed tomography (CT) or magnetic resonance imaging (MRI).

When the control system 130 is in communication with the x-ray system 151, the communication interface 140 facilitates communication of signals between the control system 130 and the x-ray device 152. This communication includes providing control commands to the x-ray source 160 and/or the x-ray detector 170 of the x-ray device 152 and receiving data from the x-ray device 152. In some embodiments, the communication interface 140 performs preliminary processing of the x-ray data prior to relaying the data to the processor 134. In examples of such embodiments, the communication interface 140 may perform amplification, filtering, and/or aggregating of the data. In an embodiment, the communication interface 140 also supplies high- and low-voltage DC power to support operation of the device 152 including circuitry within the device.

The processor 134 receives the x-ray data from the x-ray device 152 by way of the communication interface 140 and processes the data to reconstruct an image of the anatomy being imaged. The processor 134 outputs image data such that an image is displayed on the display 132. In some aspects, the processor 134 may be in communication with multiple displays. In some aspects, the intraluminal imaging system 191, intraluminal atherectomy system 101, and/or extraluminal imaging system 151 may include separate displays in addition to the display 132. The processor circuit 134, as well as processor circuits of any of the systems 191, 101, and/or 151, may output any suitable data described herein to any of the display 132, or any displays of the systems 191, 101, and/or 151. In an embodiment in which the contrast agent is introduced to the anatomy of a patient and a venogram is to be generated, the particular areas of interest to be imaged may be one or more blood vessels or other section or part of the human vasculature. The contrast agent may identify fluid filled structures, both natural and/or man-made, such as arteries or veins of a patient's vascular system, including cardiac vasculature, peripheral vasculature, neural vasculature, renal vasculature, and/or any other suitable lumen inside the body. For example, the x-ray device 152 may be used to examine any number of anatomical locations and tissue types, including without limitation all the organs, fluids, or other structures or parts of an anatomy previously mentioned. In addition to natural structures, the x-ray device 152 may be used to examine man-made structures such as any of the previously mentioned structures.

The processor 134 may be configured to receive an x-ray image that was stored by the x-ray imaging device 152 during a clinical procedure. The images may be further enhanced by other information such as patient history, patient record, IVUS imaging, pre-operative ultrasound imaging, pre-operative CT, or any other suitable data.

Figure 1C:
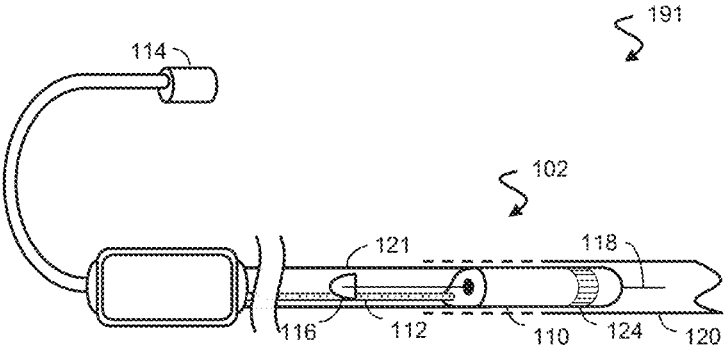
FIG. 1C is a diagrammatic view of an intraluminal imaging device, according to aspects of the present disclosure.

FIG. 1C is a diagrammatic view of an intraluminal imaging device 102, according to aspects of the present disclosure. For example, FIG. 1C illustrates aspects of the intraluminal imaging system 191, including the intraluminal imaging device 102 and related components. As described above, the intraluminal imaging system 191 may be incorporated into various systems of the broader system 100. In addition, the intraluminal imaging system 191 may include additional components than those pictured in FIG. 1C.

The intraluminal imaging system 191 can be an ultrasound imaging system. In some instances, the intraluminal imaging system 191 can be an intravascular ultrasound (IVUS) imaging system. The intraluminal imaging system 191 may include an intraluminal imaging device 102, such as a catheter, guide wire, or guide catheter, in communication with the control system 130. The control system 130 may include a display 132, a processor 134, and a communication interface 140 among other components, as described with reference to FIG. 1A. In some instances, the intravascular imaging device 102 can be an IVUS imaging device, such as a solid-state IVUS device.

At a high level, the IVUS device 102 emits ultrasonic energy from a transducer array 124 included in a scanner assembly, also referred to as an IVUS imaging assembly, mounted near a distal end of the catheter device. The ultrasonic energy is reflected by tissue structures in the surrounding medium, such as a vessel 120, or another body lumen surrounding the scanner assembly 110, and the ultrasound echo signals are received by the transducer array 124. In that regard, the device 102 can be sized, shaped, or otherwise configured to be positioned within the body lumen of a patient. The communication interface 140 transfers the received echo signals to the processor 134 of the control system 130 where the ultrasound image (including flow information in some embodiments) is reconstructed and displayed on the display 132. The control system 130, including the processor 134, can be operable to facilitate the features of the IVUS imaging system 191 described herein. For example, the processor 134 can execute computer readable instructions stored on the non-transitory tangible computer readable medium.

The communication interface 140 facilitates communication of signals between the control system 130 and the scanner assembly 110 included in the IVUS device 102. This communication includes the steps of: (1) providing commands to integrated circuit controller chip(s) included in the scanner assembly 110 to select the particular transducer array element(s), or acoustic element(s), to be used for transmit and receive, (2) providing the transmit trigger signals to the integrated circuit controller chip(s) included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) of the scanner assembly 110. In some embodiments, the communication interface 140 performs preliminary processing of the echo data prior to relaying the data to the processor 134. In examples of such embodiments, the communication interface 140 performs amplification, filtering, and/or aggregating of the data. In an embodiment, the communication interface 140 also supplies high- and low-voltage DC power to support operation of the device 102 including circuitry within the scanner assembly 110.

The processor 134 receives the echo data from the scanner assembly 110 by way of the communication interface 140 and processes the data to reconstruct an image of the tissue structures in the medium surrounding the scanner assembly 110. The processor 134 outputs image data such that an image of the lumen 120, such as a cross-sectional image of the vessel 120, is displayed on the display 132. The lumen 120 may represent fluid filled or surrounded structures, both natural and man-made. The lumen 120 may be within a body of a patient. The lumen 120 may be a blood vessel, such as an artery or a vein of a patient's vascular system, including cardiac vasculature, peripheral vasculature, neural vasculature, renal vasculature, and/or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

In some embodiments, the IVUS device includes some features similar to traditional solid-state IVUS catheters, such as the EagleEye® catheter, Visions PV 0.014P RX catheter, Visions PV 0.018 catheter, Visions PV 0.035, and Pioneer Plus catheter, each of which are available from Koninklijke Philips N.V, and those disclosed in U.S. Pat. No. 7,846,191 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors. It is understood that any suitable gauge wire can be used for the conductors. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a patient interface module (PIM) connector 114 at a proximal end of the device 102. The PIM connector 114 electrically couples the transmission line bundle 112 to the communication interface 140 and physically couples the IVUS device 102 to the communication interface 140. In some embodiments, the communication interface 140 may be a PIM. In an embodiment, the IVUS device 102 further includes a guide wire exit port 116. Accordingly, in some instances the IVUS device 102 is a rapid-exchange catheter. The guide wire exit port 116 allows a guide wire 118 to be inserted towards the distal end to direct the device 102 through the vessel 120.

In some embodiments, the intraluminal imaging device 102 may acquire intravascular images of any suitable imaging modality, including optical coherence tomography (OCT) and intravascular photoacoustic (IVPA).

Figure 1D:
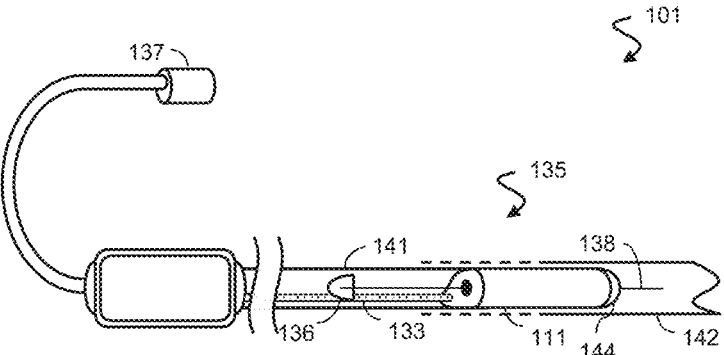
FIG. 1D is a diagrammatic view of a laser atherectomy device, according to aspects of the present disclosure.

FIG. 1D illustrates aspects of the intraluminal atherectomy system 101, including an intraluminal atherectomy device 135 and related components. As described above, the intraluminal atherectomy system 101 may be incorporated into various systems of the broader system 100. In addition, the intraluminal atherectomy system 101 may include additional components than those pictured in FIG. 1D.

The intraluminal atherectomy system 101 can be a rotational atherectomy system, such as a cutting atherectomy system, or a laser atherectomy system. The intraluminal atherectomy system 101 may include an intraluminal atherectomy system 101 may include an intraluminal atherectomy device 135. The atherectomy device 135 may include a catheter, guide wire, or guide catheter, in communication with the control system 130. The control system 130 may include a display 132, a processor 134, and a communication interface 140 among other components, as described with reference to FIG. 1A. The intraluminal atherectomy device 135 can be a laser atherectomy device.

At a high level, the atherectomy device 135 clears away obstructions within a lumen. In an example in which the atherectomy device 135 includes a rotational atherectomy device, the atherectomy device 135 may include a rotating blade at a distal end of the device. This rotating blade may contact obstructions within a vessel. As the blade contacts obstructions within the vessel, it may cut the tissue or material of the obstruction into pieces and remove the obstruction from the walls of the vessel. In some embodiments, the atherectomy catheter 135 may remove atherosclerotic plaque, medial calcium, total occlusions, soft restonotic lesions, or any other obstructions from within a lumen.

In an example in which the atherectomy device 135 includes a laser atherectomy device, the atherectomy device 135 may include an array 144 of optical fibers. The optical fibers may be disposed at a distal end of the atherectomy device 135. The optical fiber array 144 may be configured to emit ultraviolet light energy in a distal direction from the atherectomy device 135. The ultraviolet energy may be projected into the tissue directly in front of the catheter in a distal direction. The device 135 can be sized, shaped, or otherwise configured to be positioned within the body lumen of a patient. The communication interface 140 may transfer various signals to the atherectomy device 135. The control system 130, including the processor 134, can be operable to facilitate the features of the intraluminal atherectomy system 101 described herein. For example, the processor 134 can execute computer readable instructions stored on the non-transitory tangible computer readable medium.

The communication interface 140 facilitates communication of signals between the control system 130 and the assembly 111 included in the intraluminal atherectomy device 135. This communication may include the steps of: (1) providing commands to integrated circuit controller chip(s) included in the assembly 111 to select the particular optical fiber element(s) to transmit ultraviolet pulses, and/or (2) providing the transmit trigger signals to the integrated circuit controller chip(s) included in the scanner assembly 111 to activate the transmitter circuitry to generate an electrical pulse. In some embodiments, the commands to the assembly 111 of the device 135 may include specifying when to emit ultraviolet pulses. In some embodiments, the commands may also include a designation of a fluence and rate for the optical fiber array 144 and/or individual optical fibers. In an embodiment, the communication interface 140 also supplies high- and low-voltage DC power to support operation of the device 135 including circuitry within the scanner assembly 111.

The lumen 142 may represent fluid filled or surrounded structures, both natural and man-made. The lumen 142 may be within a body of a patient. The lumen 142 may be a blood vessel, such as an artery or a vein of a patient's vascular system, including cardiac vasculature, peripheral vasculature, neural vasculature, renal vasculature, and/or any other suitable lumen inside the body. For example, the device 135 may be used to clear obstructions from any locations and tissue types. In addition to natural structures, the device 135 may be used to remove obstructions from within man-made structures such as, but without limitation, heart valves, stents, shunts, filters and other devices.

In some embodiments, the atherectomy device 135 may perform photoablation. For example, the device 135 may debulk lesions and improve vessel compliance. In some aspects, a laser atherectomy device may remove obstructions while minimizing damage to the surrounding vessel in a number of ways. For example, the device 135 may perform a photochemical action in which ultraviolet light is emitted from the optical fibers of the device. This ultraviolet light may break up molecular bonds of tissue within an obstruction. These ultraviolet light pulses may be absorbed by the tissue and break down heterogenous tissues (e.g., soft tissues and hard tissues). In some embodiments, the atherectomy device 135 may also emit a sonic wave which propagates primarily parallel with the movement of the device 135. This sonic wave may oblate hard materials within the vessel with a shock wave. The atherectomy device 135 may perform a photothermal action as well which softens a lesion and may facilitate greater vessel compliance. The device 135 may also perform a photomechanical action which captures the kinetic energy created be a vapor bubble at the catheter tip. This may break through hard fibrous lesions. The vapor bubble at the tip of the device 135 may also oblate tissue turning it into smaller particles which may move downstream and be absorbed, restoring blood flow.

In some embodiments, the user of a laser atherectomy device, such as the one pictured in FIG. 1D, may reduce damage to the surrounding vessel and may reduce the risk of embolization. In some embodiments, an atherectomy device, such as the one described, may be used to create cracks or fissures in calcium deposits, or other obstructions of hard tissue, which may allow a stent reexpansion or other treatment method to expand the vessel and restore blood flow without removal of the materials of the obstruction.

In some regions of a vessel, an obstruction may prevent the guidewire 138 of the atherectomy device 135 and/or the guidewire 118 of the IVUS imaging device from passing through that region of the vessel. In such a situation, the guidewire 138 may be positioned at a position as close as possible to the obstruction in a proximal direction. The device 135 may then be moved to the same position within the vessel. In this position, directly next to and proximal of the obstruction, the atherectomy device 135 may be activated to clear a pathway through the obstruction allowing the guidewire 138 and/or the guidewire 118 to pass through the obstruction.

In some embodiments, the atherectomy device 135 described herein may include some features similar to various laser atherectomy devices, such as the Turbo-Power® atherectomy catheter, the ELCA® coronary laser atherectomy catheter, or the Turbo-Elite® laser atherectomy catheter, each of which are available from Koninklijke Philips N.V. For example, the atherectomy device 135 includes the assembly 111 near a distal end of the device 135 and an optical fiber bundle 133 extending along the longitudinal body of the device 135. The optical fiber bundle 133 can include a plurality of optical fibers, including one, two, three, four, five, six, seven, or more optical fibers. One or more optical fibers can extend from the proximal portion to the distal portion of the atherectomy device 135.

The transmission line bundle 133 terminates in a connector 137 at a proximal end of the device 135 that is configured to be coupled to light source/laser source. In some embodiments, the laser source may provide light signals and/or laser signals to be used by the laser atherectomy device 135 (e.g., the optical fibers of the device 135). In an embodiment, the atherectomy device 135 further includes a guide wire exit port 136. Accordingly, in some instances the atherectomy device 135 is a rapid-exchange catheter. The guide wire exit port 136 allows a guide wire 138 to be inserted towards the distal end to direct the device 135 through the vessel 140. In other instances, the atherectomy device 135 is an over-the-wire catheter, and the guidewire extends along all or substantially all of the length of the catheter.

Figure 1E:
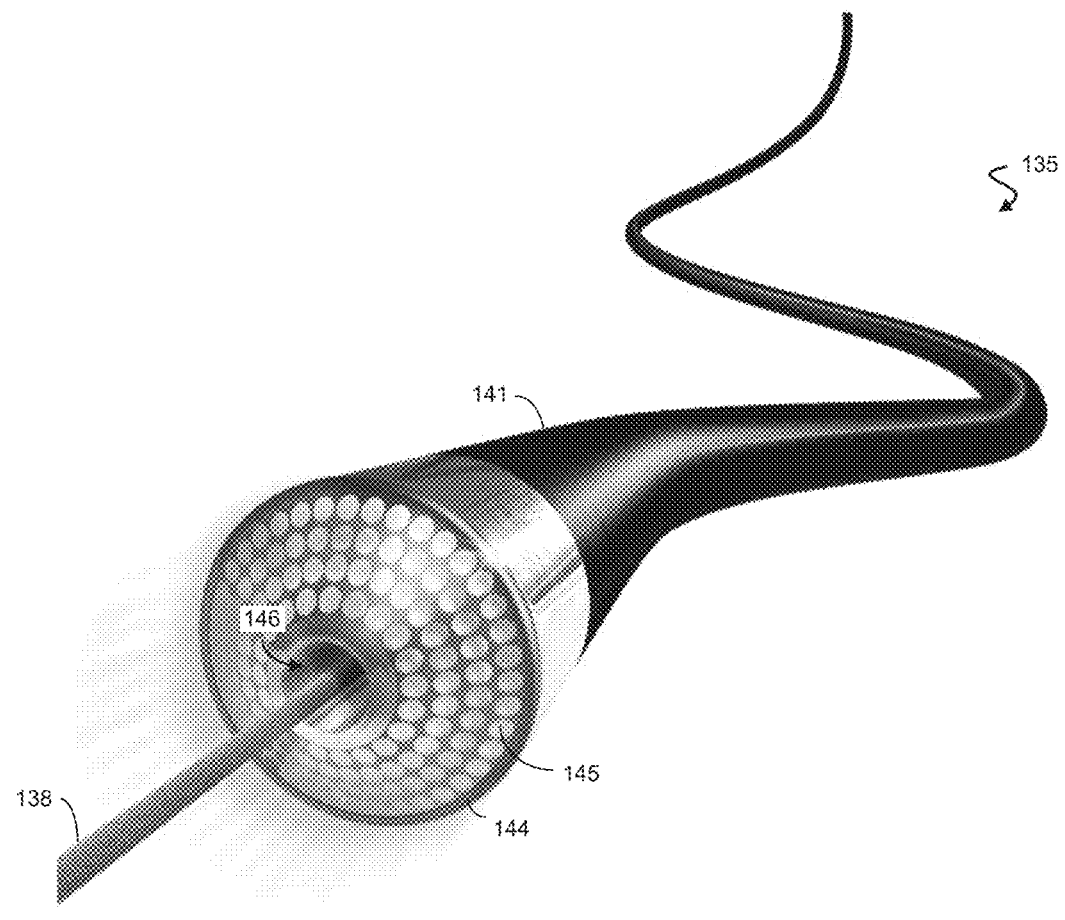
FIG. 1E is a diagrammatic view of a laser atherectomy device, according to aspects of the present disclosure.

FIG. 1E depicts an additional view of the laser atherectomy device 135, according to aspects of the present disclosure. As shown in FIG. 1E, the atherectomy device 135 may include the flexible elongate member 141. The device 135 may also be positioned around a guidewire 138, as shown. For example, the device 135 may define a lumen 146 through which the guidewire 138 may pass. In that regard, the guidewire 138 may be inserted within a vessel of a patient. The device 135 may then be inserted around the guidewire 138 and follow the guidewire 138 through the vessel to any position within the vessel.

As shown in FIG. 1E, the device 135 may include multiple optical fibers 145 within the array 144. These optical fibers 145 may positioned according to any suitable order or pattern. For example, the fibers 145 may be positioned around a circumference of the device 135 and/or the lumen 146 as shown. In other embodiments, the optical fibers 145 may alternatively be positioned only on one side of the lumen 146 and/or guidewire 138. In such an embodiment, the user may designate at which direction the device 135 may be rotated to target specific regions within a vessel.

Figure 2:
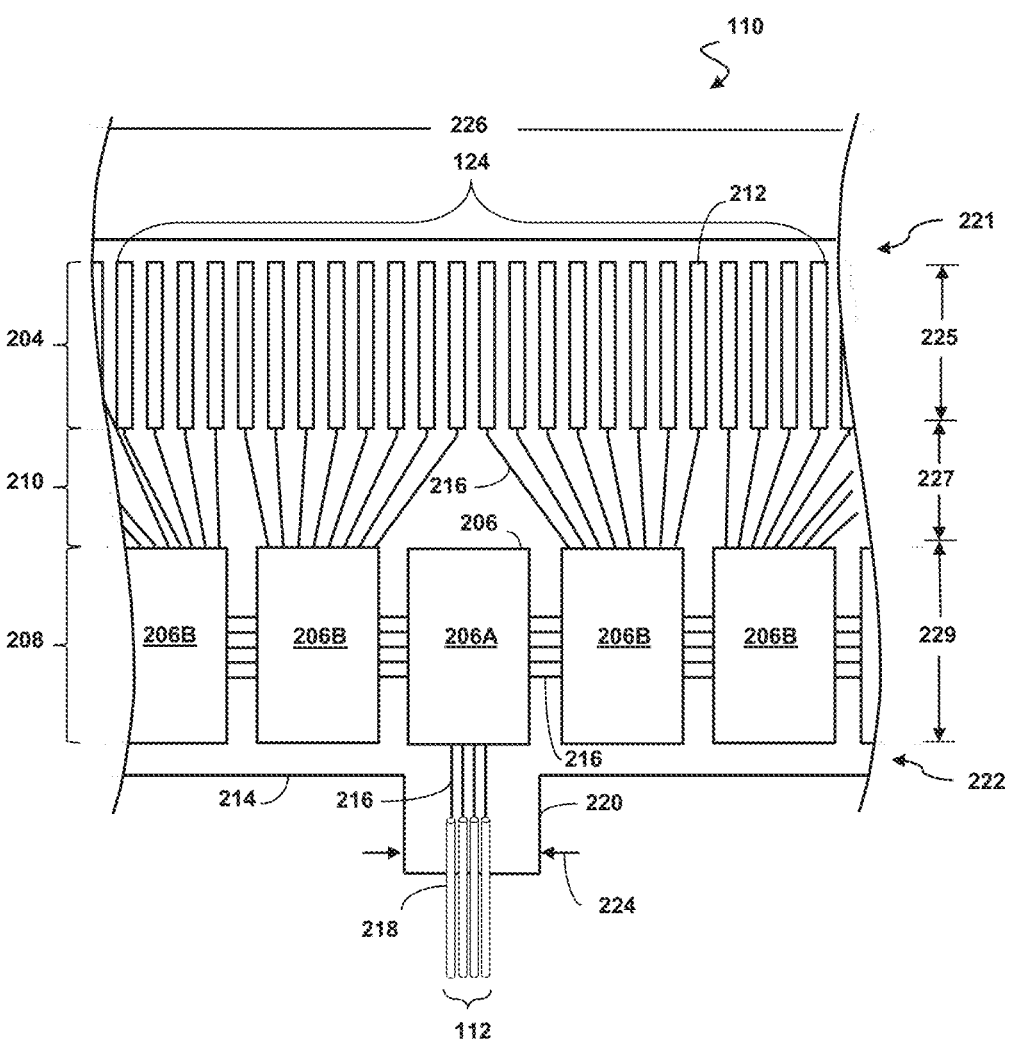
FIG. 2 is a diagrammatic top view of an ultrasound imaging assembly in a flat configuration, according to aspects of the present disclosure.

FIG. 2 is a diagrammatic top view of a portion of a flexible assembly 110, according to aspects of the present disclosure. The flexible assembly 110 may be a flexible assembly incorporated as a component of the intravascular device 102 described with reference to FIG. 1C. The flexible assembly 110 includes a transducer array 124 formed in a transducer region 204 and transducer control logic dies 206 (including dies 206A and 206B) formed in a control region 208, with a transition region 210 disposed therebetween. The transducer array 124 includes an array of ultrasound transducer elements 212. The transducer control logic dies 206 are mounted on a flexible substrate 214 into which the transducer elements 212 have been previously integrated. The flexible substrate 214 is shown in a flat configuration in FIG. 2. Though six control logic dies 206 are shown in FIG. 2, any number of control logic dies 206 may be used. For example, one, two, three, four, five, six, seven, eight, nine, ten, or more control logic dies 206 may be used.

The flexible substrate 214, on which the transducer control logic dies 206 and the transducer elements 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, liquid crystal polymer, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a support member 230 (FIG. 3) in some instances. Therefore, the thickness of the film layer of the flexible substrate 214 is generally related to the degree of curvature in the final assembled flexible assembly 110. In some embodiments, the film layer is between 5 μm and 100 μm, with some particular embodiments being between 5 μm and 25.1 μm, e.g., 6 μm.

The set of transducer control logic dies 206 is a non-limiting example of a control circuit. The transducer region 204 is disposed at a distal portion 221 of the flexible substrate 214. The control region 208 is disposed at a proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or, the length 227 of the transition region 210 may be less than lengths 225 and 229, the length 227 of the transition region 210 can be greater than lengths 225, 229 of the transducer region and controller region, respectively.

The control logic dies 206 are not necessarily homogenous. In some embodiments, a single controller is designated a master control logic die 206A and contains the communication interface for cable 112, between a processing system, e.g., processing system 106, and the flexible assembly 110. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a plurality of transducer elements 512 positioned on a transducer element 212 to emit an ultrasonic signal and selects a transducer element 212 to receive an echo. In the depicted embodiment, the master controller 206A does not directly control any transducer elements 212. In other embodiments, the master controller 206A drives the same number of transducer elements 212 as the slave controllers 206B or drives a reduced set of transducer elements 212 as compared to the slave controllers 206B. In an exemplary embodiment, a single master controller 206A and eight slave controllers 206B are provided with eight transducers assigned to each slave controller 206B.

To electrically interconnect the control logic dies 206 and the transducer elements 212, in an embodiment, the flexible substrate 214 includes conductive traces 216 formed in the film layer that carry signals between the control logic dies 206 and the transducer elements 212. In particular, the conductive traces 216 providing communication between the control logic dies 206 and the transducer elements 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 1-5 μm. For example, in an embodiment, 5 μm conductive traces 216 are separated by 5 μm of space. The width of a conductive trace 216 on the flexible substrate may be further determined by the width of the conductor 218 to be coupled to the trace or pad.

The flexible substrate 214 can include a conductor interface 220 in some embodiments. The conductor interface 220 can be in a location of the flexible substrate 214 where the conductors 218 of the cable 112 are coupled to the flexible substrate 214. For example, the bare conductors of the cable 112 are electrically coupled to the flexible substrate 214 at the conductor interface 220. The conductor interface 220 can be tab extending from the main body of flexible substrate 214. In that regard, the main body of the flexible substrate 214 can refer collectively to the transducer region 204, controller region 208, and the transition region 210. In the illustrated embodiment, the conductor interface 220 extends from the proximal portion 222 of the flexible substrate 214. In other embodiments, the conductor interface 220 is positioned at other parts of the flexible substrate 214, such as the distal portion 221, or the flexible substrate 214 may lack the conductor interface 220. A value of a dimension of the tab or conductor interface 220, such as a width 224, can be less than the value of a dimension of the main body of the flexible substrate 214, such as a width 226. In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK), nylon, Liquid Crystal Polymer (LCP), and/ or other suitable materials.

Figure 3:
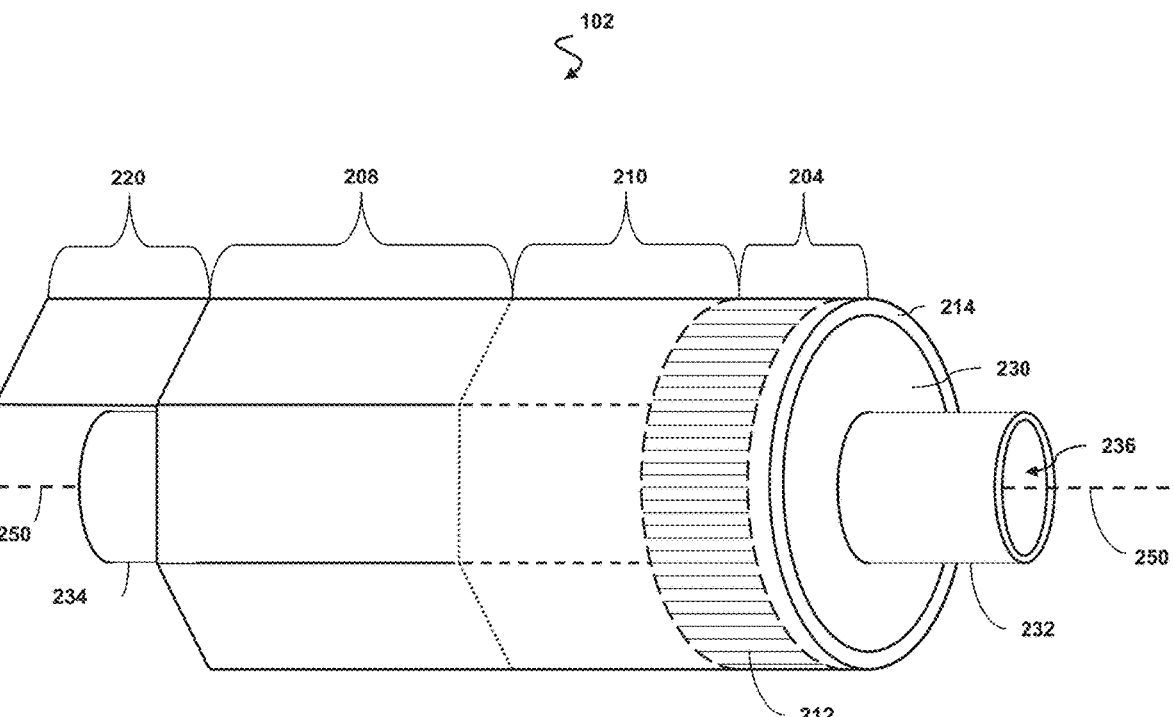
FIG. 3 is a diagrammatic perspective view of the ultrasound imaging assembly in a rolled configuration around a support member, according to aspects of the present disclosure.

FIG. 3 illustrates a perspective view of the scanner assembly 110 in a rolled configuration. The scanner assembly may be a component of the intravascular ultrasound device 102 described with reference to FIG. 1C. In some instances, the flexible substrate 214 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESO-LUTION INTRAVASCULAR ULTRASOUND SENSING ASSEMBLY HAVING A FLEXIBLE SUBSTRATE," each of which is hereby incorporated by reference in its entirety.

Depending on the application and embodiment of the presently disclosed invention, transducer elements 212 may be piezoelectric transducers, single crystal transducer, or PZT (lead zirconate titanate) transducers. In other embodiments, the transducer elements of transducer array 124 may be flexural transducers, piezoelectric micromachined ultrasonic transducers (PMUTs), capacitive micromachined ultrasonic transducers (CMUTs), or any other suitable type of transducer element. In such embodiments, transducer elements 212 may comprise an elongate semiconductor material or other suitable material that allows micromachining or similar methods of disposing extremely small elements or circuitry on a substrate.

In some embodiments, the transducer elements 212 and the controllers 206 can be positioned in an annular configuration, such as a circular configuration or in a polygon configuration, around a longitudinal axis 250 of a support member 230. It is understood that the longitudinal axis 250 of the support member 230 may also be referred to as the longitudinal axis of the scanner assembly 110, the flexible elongate member 121, or the device 102. For example, a cross-sectional profile of the imaging assembly 110 at the transducer elements 212 and/or the controllers 206 can be a circle or a polygon. Any suitable annular polygon shape can be implemented, such as one based on the number of controllers or transducers, flexibility of the controllers or transducers, etc. Some examples may include a pentagon, hexagon, heptagon, octagon, nonagon, decagon, etc. In some examples, the transducer controllers 206 may be used for controlling the ultrasound transducers 512 of transducer elements 212 to obtain imaging data associated with the vessel 120.

The support member 230 can be referenced as a unibody in some instances. The support member 230 can be composed of a metallic material, such as stainless steel, or a non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. In some embodiments, support member 230 may be composed of 303 stainless steel. The support member 230 can be a ferrule having a distal flange or portion 232 and a proximal flange or portion 234. The support member 230 can be tubular in shape and define a lumen 236 extending longitudinally therethrough. The lumen 236 can be sized and shaped to receive the guide wire 118. The support member 230 can be manufactured using any suitable process. For example, the support member 230 can be machined and/or electrochemically machined or laser milled, such as by removing material from a blank to shape the support member 230, or molded, such as by an injection molding process or a micro injection molding process.

Figure 4:
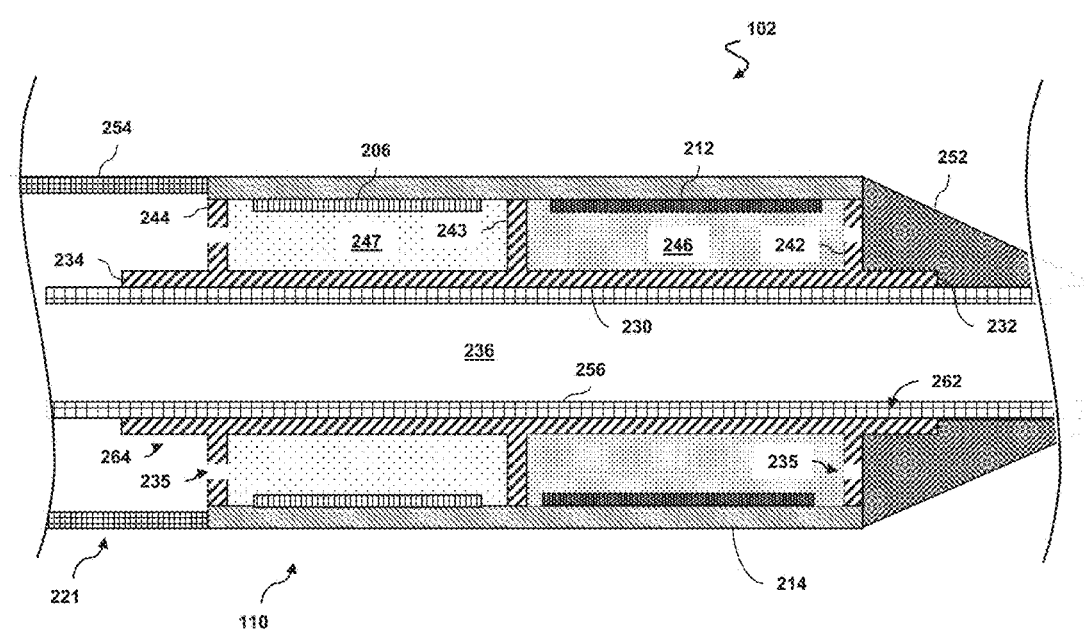
FIG. 4 is a diagrammatic cross-sectional side view of the ultrasound imaging assembly, according to aspects of the present disclosure.

Referring now to FIG. 4, shown therein is a diagrammatic cross-sectional side view of a distal portion of the intraluminal imaging device 102, including the flexible substrate 214 and the support member 230, according to aspects of the present disclosure. The lumen 236 may be connected with the entry/exit port 116 and is sized and shaped to receive the guide wire 118 (FIG. 1). In some embodiments, the support member 230 may be integrally formed as a unitary structure, while in other embodiments the support member 230 may be formed of different components, such as a ferrule and stands 242, 243, and 244, that are fixedly coupled to one another. In some cases, the support member 230 and/or one or more components thereof may be completely integrated with inner member 256. In some cases, the inner member 256 and the support member 230 may be joined as one, e.g., in the case of a polymer support member.

Stands 242, 243, and 244 that extend vertically are provided at the distal, central, and proximal portions respectively, of the support member 230. The stands 242, 243, and 244 elevate and support the distal, central, and proximal portions of the flexible substrate 214. In that regard, portions of the flexible substrate 214, such as the transducer portion 204 (or transducer region 204), can be spaced from a central body portion of the support member 230 extending between the stands 242, 243, and 244. The stands 242, 243, 244 can have the same outer diameter or different outer diameters. For example, the distal stand 242 can have a larger or smaller outer diameter than the central stand 243 and/or proximal stand 244 and can also have special features for rotational alignment as well as control chip placement and connection.

To improve acoustic performance, the cavity between the transducer array 212 and the surface of the support member 230 may be filled with an acoustic backing material 246. The liquid backing material 246 can be introduced between the flexible substrate 214 and the support member 230 via passageway 235 in the stand 242, or through additional recesses as will be discussed in more detail hereafter. The backing material 246 may serve to attenuate ultrasound energy emitted by the transducer array 212 that propagates in the undesired, inward direction.

The cavity between the circuit controller chips 206 and the surface of the support member 230 may be filled with an underfill material 247. The underfill material 247 may be an adhesive material (e.g. an epoxy) which provides structural support for the circuit controller chips 206 and/or the flexible substrate 214. The underfill 247 may additionally be any suitable material.

In some embodiments, the central body portion of the support member can include recesses allowing fluid communication between the lumen of the unibody and the cavities between the flexible substrate 214 and the support member 230. Acoustic backing material 246 and/or underfill material 247 can be introduced via the cavities (during an assembly process, prior to the inner member 256 extending through the lumen of the unibody. In some embodiments, suction can be applied via the passageways 235 of one of the stands 242, 244, or to any other suitable recess while the liquid backing material 246 is fed between the flexible substrate 214 and the support member 230 via the passageways 235 of the other of the stands 242, 244, or any other suitable recess. The backing material can be cured to allow it to solidify and set. In various embodiments, the support member 230 includes more than three stands 242, 243, and 244, only one or two of the stands 242, 243, 244, or none of the stands. In that regard the support member 230 can have an increased diameter distal portion 262 and/or increased diameter proximal portion 264 that is sized and shaped to elevate and support the distal and/or proximal portions of the flexible substrate 214.

The support member 230 can be substantially cylindrical in some embodiments. Other shapes of the support member 230 are also contemplated including geometrical, non-geometrical, symmetrical, non-symmetrical, cross-sectional profiles. As the term is used herein, the shape of the support member 230 may reference a cross-sectional profile of the support member 230. Different portions of the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can comprise a flexible elongate member. The proximal inner member 256 can be received within a proximal flange 234. The proximal outer member 254 abuts and is in contact with the proximal end of flexible substrate 214. A distal tip member 252 is coupled to the distal portion 262 of the support member 230. For example, the distal member 252 is positioned around the distal flange 232. The tip member 252 can abut and be in contact with the distal end of flexible substrate 214 and the stand 242. In other embodiments, the proximal end of the tip member 252 may be received within the distal end of the flexible substrate 214 in its rolled configuration. In some embodiments there may be a gap between the flexible substrate 214 and the tip member 252. The distal member 252 can be the distal-most component of the intraluminal imaging device 102. The distal tip member 252 may be a flexible, polymeric component that defines the distal-most end of the imaging device 102. The distal tip member 252 may additionally define a lumen in communication with the lumen 236 defined by support member 230. The guide wire

118 may extend through lumen 236 as well as the lumen defined by the tip member 252.

One or more adhesives can be disposed between various components at the distal portion of the intraluminal imaging device 102. For example, one or more of the flexible substrate 214, the support member 230, the distal member 252, the proximal inner member 256, the transducer array 212, and/or the proximal outer member 254 can be coupled to one another via an adhesive. Stated differently, the adhesive can be in contact with e.g. the transducer array 212, the flexible substrate 214, the support member 230, the distal member 252, the proximal inner member 256, and/or the proximal outer member 254, among other components.

Figure 5:
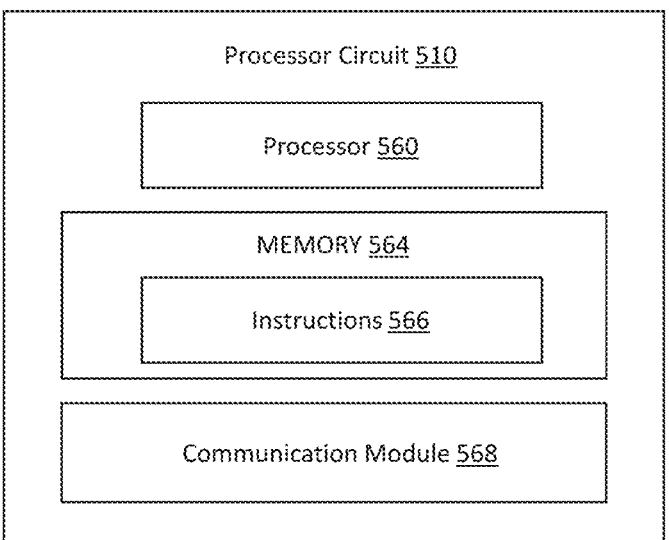
FIG. 5 is a schematic diagram of a processor circuit, according to aspects of the present disclosure.

FIG. 5 is a schematic diagram of a processor circuit, according to aspects of the present disclosure. The processor circuit 510 may be implemented in the control system 130 of FIG. 1A, the intraluminal imaging system 191, the physiology measurement system 101, and/or the x-ray imaging system 151, or any other suitable location. In an example, the processor circuit 510 may be in communication with intraluminal imaging device 102, the x-ray imaging device 152, the intraluminal atherectomy device 135, and/or the display 132 within the system 100. The processor circuit 510 may include the processor 134 and/or the communication interface 140 (FIG. 1A). One or more processor circuits 510 are configured to execute the operations described herein. As shown, the processor circuit 510 may include a processor 560, a memory 564, and a communication module 568. These elements may be in direct or indirect communication with each other, for example via one or more buses.

The processor 560 may include a CPU, a GPU, a DSP, an application-specific integrated circuit (ASIC), a controller, an FPGA, another hardware device, a firmware device, or any combination thereof configured to perform the operations described herein. The processor 560 may also be implemented as a combination of computing devices, e.g., a combination of a DSP and a microprocessor, a plurality of microprocessors, one or more microprocessors in conjunction with a DSP core, or any other such configuration.

The memory 564 may include a cache memory (e.g., a cache memory of the processor 560), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 564 includes a non-transitory computer-readable medium. The memory 564 may store instructions 566. The instructions 566 may include instructions that, when executed by the processor 560, cause the processor 560 to perform the operations described herein with reference to the probe 110 and/or the host 130 (FIG. 1). Instructions 566 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 568 can include any electronic circuitry and/or logic circuitry to facilitate direct or indirect communication of data between the processor circuit 510, the probe 110, and/or the display 132 and/or display 132. In that regard, the communication module 568 can be an input/output (I/O) device. In some instances, the communication module 568 facilitates direct or indirect communication between various elements of the processor circuit 510 and/or the probe 110 (FIG. 1) and/or the host 130 (FIG. 1).

Figure 6:
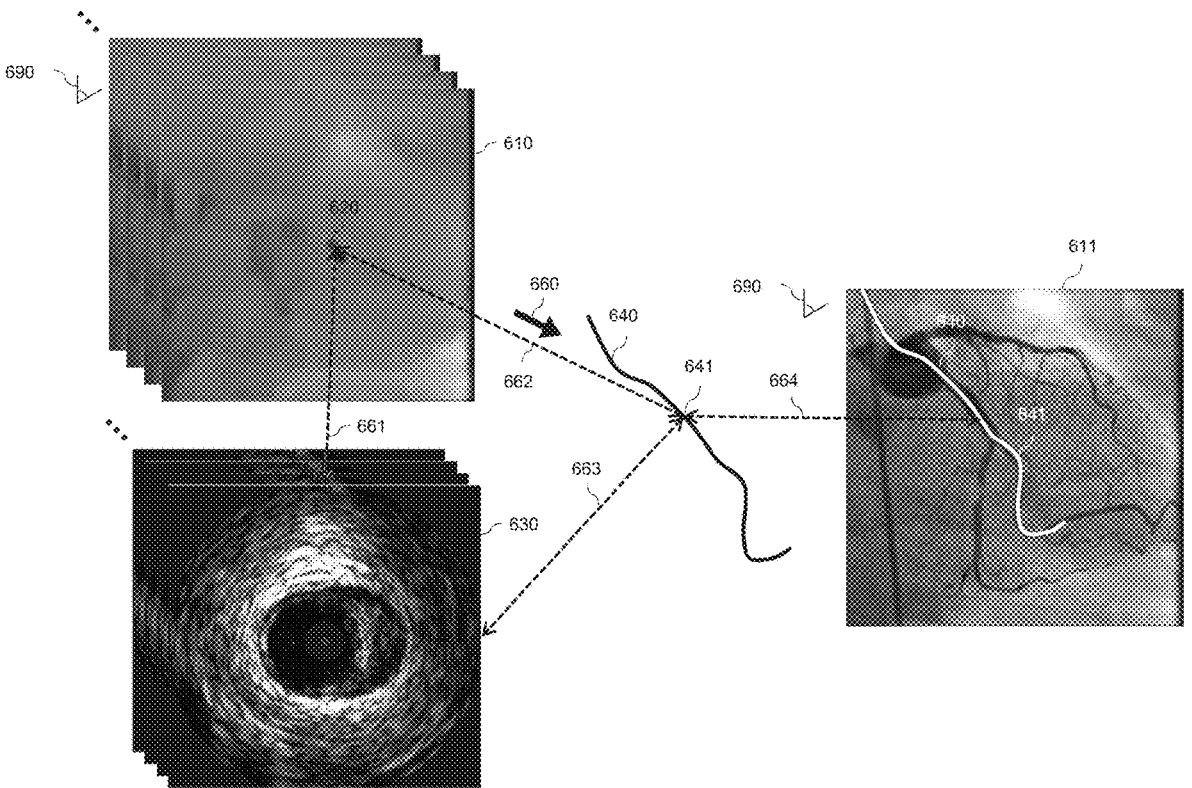
FIG. 6 is a diagrammatic view of a relationship between x-ray fluoroscopy images, intravascular data, and a path defined by the motion of an intravascular device, according to aspects of the present disclosure.

FIG. 6 is a diagrammatic view of a relationship between x-ray fluoroscopy images 610, intravascular data 630, and a path 640 defined by the motion of an intravascular device 620, according to aspects of the present disclosure. FIG. 6 describes a method of coregistering intravascular data 630 including intravascular images with corresponding locations on one or more fluoroscopy images 610 of the same region of a patient's anatomy. As will be described in more detail hereafter, the intravascular data 630 may additionally include data such as the identification or classification of various tissue within an IVUS image, a cross-sectional area of each or all of the various tissue, extent of tissue as a percentage or ratio, a recommended atherectomy status including an on or off instruction, a fluence setting, a rate setting, or any other data. Co-registration may include the process of associating two data elements with each other in a memory, for example, in the memory 564 of the processor circuit 510. For example, an IVUS image may be one data element which is associated with a location within a fluoroscopy image, which is another data element. In another example, a laser atherectomy setting may be associated with an IVUS image and/or a location within a fluoroscopy image. Associations of any of the other types of data described herein is similarly expected.

The patient anatomy may be imaged with an x-ray device while a physician performs a pullback with an intravascular device 620, e.g., while the intravascular device 620 moves through a blood vessel of the anatomy. The intravascular device may be substantially similar to the intravascular device 102 described with reference to FIG. 1C. The x-ray device used to obtain the fluoroscopy images 610 may be substantially similar to the x-ray device 152 of FIG. 1B. In some embodiments, the fluoroscopy images 610 may be obtained while no contrast agent is present within the patient vasculature. Such an embodiment is shown by the fluoroscopy images 610 in FIG. 6. The radiopaque portion of the intravascular device 620 is visible within the fluoroscopy image 610. The fluoroscopy images 610 may correspond to a continuous image stream of fluoroscopy images and may be obtained as the patient anatomy is exposed to a reduced dose of x-radiation. It is noted that the fluoroscopy images 610 may be acquired with the x-ray source 160 and the x-ray detector 170 positioned at any suitable angle in relation to the patient anatomy. This angle is shown by angle 690.

The intravascular device 620 may be any suitable intravascular device. As the intravascular device 620 moves through the patient vasculature, the x-ray imaging system may acquire multiple fluoroscopy images 610 showing the radiopaque portion of the intravascular device 620. In this way, each fluoroscopy image 610 shown in FIG. 6 may depict the intravascular device 620 positioned at a different location such that a processor circuit may track the position of the intravascular device 620 over time.

As the intravascular device 620 is pulled through the patient vasculature, it may acquire intravascular data 630. In an example, the intravascular data 630 shown in FIG. 6 may be IVUS images. However, the intravascular data may be any suitable data, including IVUS images, FFR data, iFR data, OCT images, intravascular photoacoustic (IVPA) images, or any other measurements or metrics relating to blood pressure, blood flow, lumen structure, or other physiological data acquired during a pullback of an intravascular device.

As the physician pulls the intravascular device 620 through the patient vasculature, each intravascular data point 630 acquired by the intravascular device 620 may be associated with a position within the patient anatomy in the fluoroscopy images 610, as indicated by the arrow 661. For example, the first IVUS image 630 shown in FIG. 6 may be associated with the first fluoroscopy image 610. The first IVUS image 630 may be an image acquired by the intravascular device 620 at a position within the vasculature, as depicted in the first fluoroscopy image 610 as shown by the intravascular device 620 within the image 610. Similarly, an additional IVUS image 630 may be associated with an additional fluoroscopy image 610 showing the intravascular device 620 at a new location within the image 610, and so on. The processor circuit may determine the locations of the intravascular device 620 within each acquired x-ray image 610 by any suitable method. For example, the processor circuit may perform various image processing techniques, such as edge identification of the radiopaque marker, pixel-by-pixel analysis to determine transition between light pixels and dark pixels, filtering, or any other suitable techniques to determine the location of the imaging device 620. In some embodiments, the processor circuit may use various artificial intelligence methods including deep learning techniques such as neural networks or any other suitable techniques to identify the locations of the imaging device 620 within the x-ray images 610.

Any suitable number of IVUS images or other intravascular data points 630 may be acquired during an intravascular device pullback and any suitable number of fluoroscopy images 610 may be obtained. In some embodiments, there may be a one-to-one ratio of fluoroscopy images 610 and intravascular data 630. In other embodiments, there may be differing numbers of fluoroscopy images 610 and/or intravascular data 630. The process of co-registering the intravascular data 630 with one or more x-ray images may include some features similar to those described in U.S. Pat. No. 7,930,014, titled, "VASCULAR IMAGE CO-REGISTRATION," and filed Jan. 11, 2006, which is hereby incorporated by reference in its entirety. The co-registration process may also include some features similar to those described in U.S. Pat. Nos. 8,290,228, 8,463,007, 8,670,603, 8,693,756, 8,781,193, 8,855,744, and 10,076,301, all of which are also hereby incorporated by reference in their entirety.

The system 100 may additionally generate a fluoroscopy-based 2D pathway 640 defined by the positions of the intravascular device 620 within the x-ray fluoroscopy images 610. The different positions of the intravascular device 620 during pullback, as shown in the fluoroscopy images 610, may define a two-dimensional pathway 640, as shown by the arrow 660. The fluoroscopy-based 2D pathway 640 reflects the path of one or more radiopaque portions of the intravascular device 620 as it moved through the patient vasculature as observed from the angle 690 by the x-ray imaging device 152. The fluoroscopy-based 2D pathway 640 defines the path as measured by the x-ray device which acquired the fluoroscopy images 610, and therefore shows the path from the same angle 690 at which the fluoroscopy images were acquired. Stated differently, the 2D pathway 640 describes the projection of the 3D path followed by the device onto the imaging plane at the imaging angle 690. In some embodiments, the pathway 640 may be determined by an average of the detected locations of the intravascular device 620 in the fluoroscopy images 610. For example, the pathway 640 may not coincide exactly with the guidewire in any fluoroscopy image 610 selected for presentation.

As shown by the arrow 662, because the two-dimensional path 640 is generated based on the fluoroscopy images 610, each position along the two-dimensional path 640 may be associated with one or more fluoroscopy images 610. As an example, at a location 641 along the path 640, the first fluoroscopy image 610 may depict the intravascular device 620 at that same position 641. In addition, because a correspondence was also established between the fluoroscopy images 610 and the intravascular data 630 as shown by the arrow 661, intravascular data 630, such as the first IVUS image shown, may also be associated with the location 641 along the path 640 as shown by the arrow 663.

Finally, the path 640 generated based on the locations of the intravascular device 620 within the fluoroscopy images 610 may be overlaid onto any suitable fluoroscopy image 611 (e.g., one of the fluoroscopic images 610 in the fluoroscopic image stream). In this way, any location along the path 640 displayed on the fluoroscopy image 611 may be associated with IVUS data such as an IVUS image 630, as shown by the arrow 664. For example, IVUS image 630 shown in FIG. 6 may be acquired simultaneously with the fluoroscopy image 610 shown and the two may be associated with each other as shown by the arrow 661. The fluoroscopy image 610 may then indicate the location of the intravascular device 620 along the path 640, as shown by the arrow 662, thus associating the IVUS image 630 with the location 641 along the path 640 as shown by the arrow 663. Finally, the IVUS image 630 may be associated with the location within the fluoroscopy image 610 at which it was acquired by overlaying the path 640 with associated data on the fluoroscopy image 611. The pathway 640 itself may or may not be displayed on the image 611.

In the illustrated embodiment of FIG. 6, the co-registered IVUS images are associated with one of the fluoroscopic images obtained without contrast such that that the position at which the IVUS images are obtained is known relative to locations along the guidewire. In other embodiments, the co-registered IVUS images are associated with an x-ray image obtained with contrast (in which the vessel is visible) such that that the position at which the IVUS images are obtained is known relative to locations along the vessel.

Figure 7:
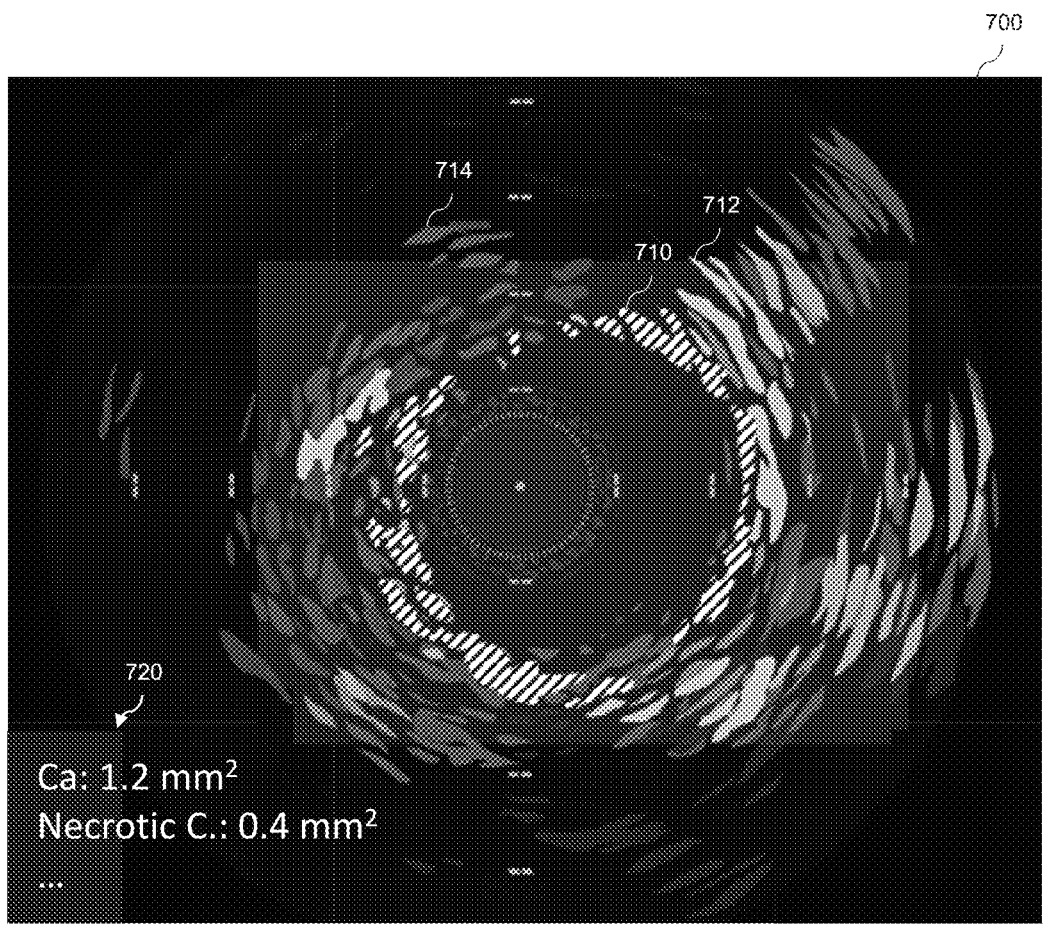
FIG. 7 is a diagrammatic view of an intravascular ultrasound image, according to aspects of the present disclosure.

FIG. 7 is a depiction of an IVUS image 700, according to aspects of the present disclosure. In some embodiments, the IVUS image 700 may include depictions of different types of tissues or other structures within the image.

In some aspects, the processor circuit 510 may be configured to automatically classify different tissues observed in the image 700. For example, in some embodiments, the processor circuit 510 may be configured to implement various algorithms to automatically classify regions of the image 700. In one embodiment, the processor circuit 510 may implement a machine learning network.

In an embodiment in which the processor circuit 510 implements a machine learning network, the machine learning network may include a deep learning network. The deep learning network may be trained to identify the locations of various tissues within an IVUS image. For example, the network may be trained to identify regions corresponding to plaque, calcified deposits (e.g., calcium), dense calcium, fibrous tissues, fibro-fatty tissues, lipids, complex carbohydrates, necrotic core, various blood cells, dead blood cells, muscle cells, or any other materials. In the example shown in FIG. 7, the processor circuit 510 may be configured to identify different materials observed within the IVUS image 700 with varying colors, shading, or patterns. For example, the regions 710 shown in FIG. 7 may correspond to identified calcium within the image 700. The shaded regions 712 and 714 may correspond to other identified tissue types.

In some embodiments, a vessel border, lumen border, and/or stent border may also be identified by the deep learning network. In some embodiments, the vessel border, lumen border, and/or stent border are identified by a user and received by the processor circuit 510. In some embodiments, the lumen border may be the inner edge of the vessel wall. The lumen border may define the lumen. The machine learning algorithm 700 may be trained to identify the vessel border, lumen border, and/or stent edge. The processor circuit 510 may be configured to recognize the boundaries of the vessel within the ultrasound image as well as the boundaries of the lumen and/or stent. By providing the user of the system 100 with a representation of the vessel border, lumen border, and/or stent edge, the user may more accurately determine the severity of an obstruction or restenosis within the vessel and more accurately select a treatment method.

Examples of border detection, image processing, image analysis, and/or pattern recognition include U.S. Pat. No. 6,200,268 entitled "VASCULAR PLAQUE CHARACTER-IZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARAC-TERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYS-TEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETEC-TION" issued Dec. 9, 2008 with Jon D. Klingensmith, Anuja Nair, Barry D. Kuban and D. Geoffrey Vince, as inventors, the teachings of which are hereby incorporated by reference herein in their entirety.

As shown by the metrics 720 of FIG. 7, the extent or presence of any of the tissues identified in an IVUS image, such as the image 700, may be quantified in any suitable way. For example, any calcium deposits detected within the image 700 may be associated with a cross-sectional area of the deposits. Similarly, the cross-sectional area of any other material or tissue observed within the image 700 may be calculated and displayed as well. In some embodiments, the presence of any particular material or tissue within an image 700 may be quantified as a percentage, ratio, or by any other metrics. For example, the cross-sectional area of a material, such as calcium, may be compared with the cross-sectional area of the vessel, for example, and conveyed as a percentage or ratio.

Figure 8:
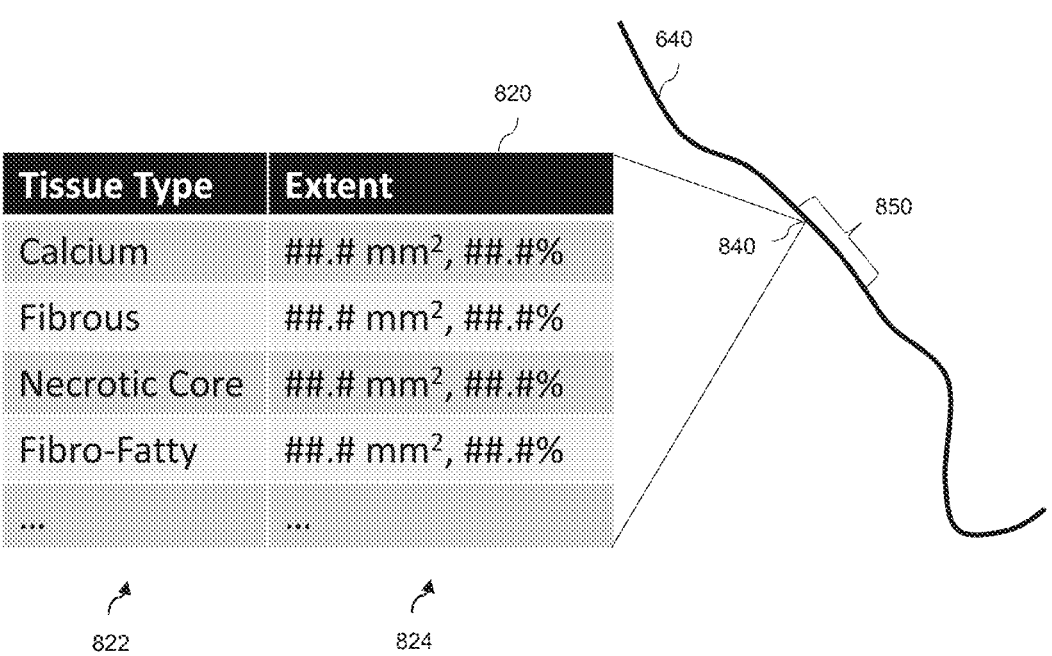
FIG. 8 is a diagrammatic view of intravascular ultrasound data coregistered to a device pathway, according to aspects of the present disclosure.

FIG. 8 is a diagrammatic view of intravascular ultrasound data coregistered to a device pathway 640, according to aspects of the present disclosure. Similar to the metrics 720 of FIG. 7, the metrics 820 shown in FIG. 8 may include a list of any types of tissue or materials automatically identified by the processor circuit 510 in one individual IVUS image. In some embodiments, the metrics 820 may correspond to multiple IVUS images such as IVUS images along a section of the pathway 640 or region of the vessel or along the entire imaged section of a vessel.

In the example shown in FIG. 8, the metrics 820 may correspond to a single IVUS image obtained at the location 840 shown along the pathway 640. This location may correspond to the presence of any of the types of tissue or material listed previously. Some of these tissues and/or materials are shown in FIG. 8 as materials 822. For example, this location 840 may correspond to a cross-sectional radial view of the vessel with observed calcium, fibrous tissues, necrotic core, lipid tissues, and other materials or tissues 822. The cross-sectional areas 824 of each of these materials and/or tissues 822 may be calculated, associated with their respective tissue or material type, and displayed to a user and/or stored in a memory in communication with the processor circuit 510.

Based on these measurements 822 and 824, the processor circuit 510 may identify regions along the vessel and/or path 640 corresponding to an increased presence of obstructive material, such as the region 850 shown in FIG. 8. The processor circuit 510 may select IVUS images and/or corresponding locations along the path 640 as part of a region 850 according to any suitable method. For example, in some embodiments, a threshold cross-sectional area, as either an area metric, percentage metric, or ratio metric may be determined for any of the materials 822 or all materials 822 as a whole. For example, a threshold of 25% of all combined obstructive tissue or material types may be determined as a threshold. In such an example, any IVUS images in which all materials 822 combined add up to 25% of the vessel cross-sectional area may be selected as IVUS images and/or locations along the path 640 to be included in the region 850. A threshold related to only a calcium type may additionally or alternatively be selected or a threshold related to any other material or tissue or combinations may be selected.

In some embodiments, the processor circuit 510 may select IVUS images and/or locations along the path 640 for inclusion into a region 850 by implementations of a machine learning network. For example, the machine learning network may be trained to identify IVUS images related to an increased likelihood of complications and select these images to be included in one or more regions 850. In some embodiments, the machine learning network may be trained by receiving multiple annotated IVUS images annotated by experts in the field.

Figure 9:
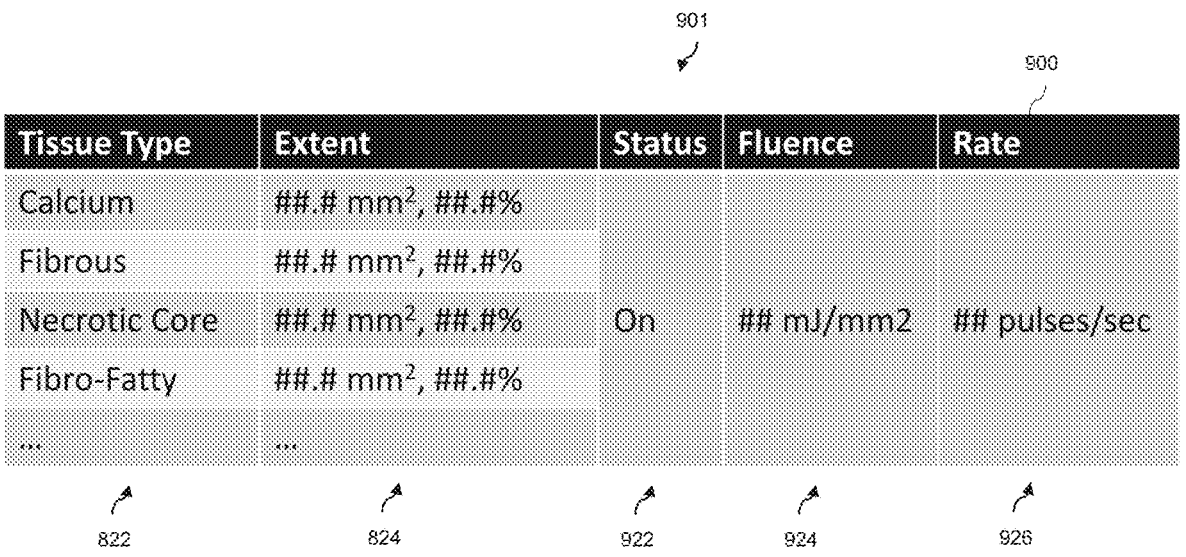
FIG. 9 is a diagrammatic view of atherectomy device settings associated with intravascular ultrasound data, according to aspects of the present disclosure.

FIG. 9 is a diagrammatic view of atherectomy device settings 901 associated with intravascular ultrasound data, according to aspects of the present disclosure. In the example shown in FIG. 9, the table 900 may correspond to the image 700 described with reference to FIG. 7. In some embodiments, the table 900 may include the list of tissue or material types 822 automatically identified within an IVUS image and the cross-sectional area metrics 824 associated with each type of tissue or material 822. In addition, the table 900 may include a recommended status 922 corresponding to the atherectomy device 135 as well as a recommended fluence setting 924 of the device 135 and a recommended pulse rate 926 of the device 135.

Any of the data 901 shown in the table 900 may be associated with an IVUS image corresponding to a location along the path 640. In some embodiments, the recommended status 922, fluence setting 924, and rate setting 926 of the atherectomy device 135 may be determined by the processor circuit 510 based on the tissue type data 822 and corresponding extent data 824.

In one example, the processor circuit 510 may determine the data 922, 924, and 926 by comparing the tissue type 822 and/or extent data 824 with various thresholds as has been previously described.

In one example, the processor circuit 510 may determine the data 922, 924, and 926 by comparing the tissue type 822 and/or extent data 824 with recommended settings associated with various tissue types 822 and extent data 824. For example, the processor circuit 510 may retrieve from a memory an additional collection of data, such as a table, including a list of recommended statuses 922, fluence settings 924, and pulse rates 926.

In one embodiment, the processor circuit 510 may access a collection of data which associates ranges of cross-sectional areas, percentages, and/or ratios of calcium with a recommended statuses, fluence settings, and rate settings. For example, it may be recommended to start with lower settings, e.g., 30 (fluency)/20 (rate) with a 1.4 mm catheter using a saline infusion technique. On the other hand, for ISR, it may be recommended to start with the highest setting, e.g., 80/80. In another example, a range of 0.0%-5.0% obstruction (e.g., all tissue types 822 of the obstructions combined correspond to 0.0%-5.0% of the cross-sectional area of the vessel) may be associated with a recommended atherectomy device status of "Off", meaning e.g., it is not recommended that the atherectomy device 135 be used at that location. In another example, a range of 25.0%-35.0% obstruction with a calcium content percentage of 10.0%-20.0% may be associated with a recommended device status of "On" with a recommended 60 mJ/mm² fluence and a pulse rate of 70 pulses/second. Any other ranges and recommended settings may be included in the data or table in communication with the processor circuit 510. These recommended settings may be compiled by experts in the field, may be determined based on past atherectomy procedures of the same patient, different patients, or any other data. In some embodiments, the processor circuit 510 may determine these recommended values based on patient data stored in a memory.

In one example, the processor circuit 510 may determine the data 922, 924, and 926 by implementing a machine learning network algorithm, such as any of the machine learning network algorithms previously described.

It is noted that the steps shown and described with reference to FIG. 9, including determining laser atherectomy settings for particular positions along the vessel based on the IVUS images of those positions, may be performed at any suitable stage of the procedure. For example, IVUS images received during an imaging procedure may be analyzed in real time such that recommended laser atherectomy settings are calculated as IVUS images are received. In some aspects, the IVUS images may be analyzed to determine corresponding laser atherectomy settings only after all IVUS images are received. In that regard, when a laser atherectomy setting is determined based on an IVUS image, the setting may be associated (e.g., by co-registration) with the IVUS image in the memory. Similarly, the laser atherectomy setting may be associated (e.g., by co-registration) with a location within a fluoroscopy image, such a set of pixel coordinates identifying a location within a fluoroscopy image, or a location along a length of the vessel. In that regard, at a later laser atherectomy procedure, as the position of the laser atherectomy device is tracked through the vessel, the laser atherectomy setting previously calculated and associated with the position may be recalled from the memory and applied.

In some aspects, the IVUS images may be analyzed to determine corresponding laser atherectomy settings during a laser atherectomy procedure. For example, as a laser atherectomy device is moved to a particular position within the vessel, the corresponding IVUS image may be analyzed to determine the recommended laser atherectomy setting for the position of the device at that time.

Figure 10:
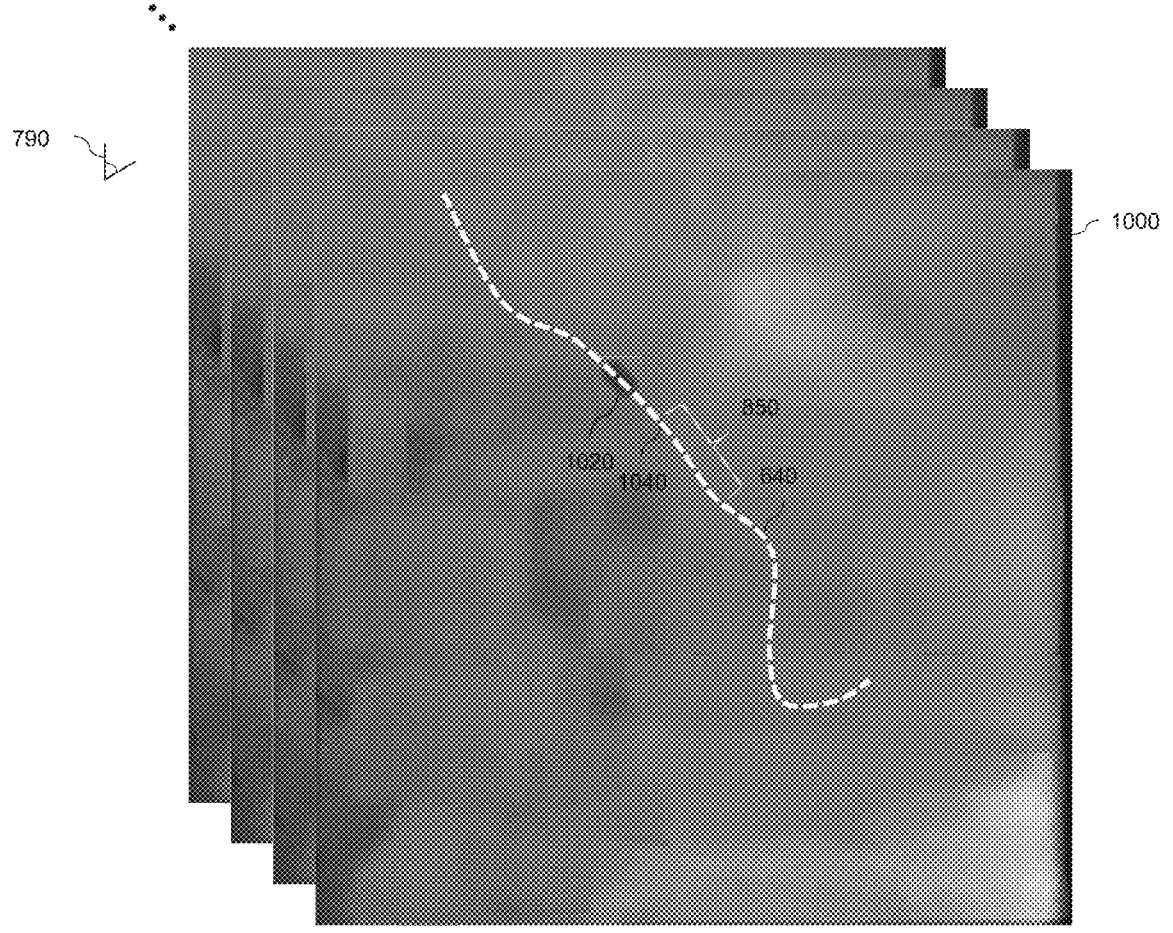
FIG. 10 is a diagrammatic view of extraluminal images, according to aspects of the present disclosure.

FIG. 10 is a diagrammatic view of extraluminal images 1000, according to aspects of the present disclosure. The images 1000 may be x-ray images, such as fluoroscopy images or angiography images obtained during an atherectomy procedure. In some embodiments, the images 1000, including any of the elements overlaid over the image 1000, may be displayed to a user during an atherectomy procedure or may not be.

The images 1000 may include a depiction of a radiopaque portion of an atherectomy device 1020. The atherectomy device 1020 may be substantially similar to the atherectomy device 135 described with reference to FIG. 1D. In some embodiments, the atherectomy device 1020 may include a radiopaque portion.

In some embodiments and as shown in FIG. 10, the images 1000 may also include a depiction of a guidewire. The guidewire may be substantially similar to the guidewire of FIG. 1D. For example, the atherectomy device 1020 may be disposed around the guidewire. The atherectomy device 1020 may be moved along the guidewire through the vessel. In some embodiments, the shape of the vessel to be treated may be identified within the image 1000 by the guidewire. In other embodiments, the vessel may be identified by a contrast agent within the vessel or by other landmarks associated with the vessel and visible within the images 1000.

In some embodiments, the pathway 640 may be displayed adjacent to a depiction of the treated vessel. The pathway 640 may be the same pathway generated with reference to FIG. 6 corresponding to the movement of the IVUS imaging device during a previous IVUS imaging procedure. In this case, each location along the pathway 640 may correspond to one or more IVUS images and one or data sets, such as the data 901 described with reference to FIG. 9. For example, each location along the pathway 640 may correspond to a list of tissues or materials automatically identified within an IVUS image obtained at that location, a metric conveying the extent of that tissue or material (e.g., a cross-sectional area, percentage, or ratio), and a recommended atherectomy device status and accompanying recommended fluence and pulse rate settings. In some embodiments, regions of increased obstruction, such as the region 850 previously described with reference to FIG. 8, may also be identified along the pathway 640 and/or the vessel in the image 1000.

In some embodiments, during an atherectomy procedure, the atherectomy device 1020 may be positioned within the vessel to be treated. Because the atherectomy procedure may performed while extraluminal images, such as the images 1000, are obtained, the device 1020 may be observed in real time by the user of the system within the images 1000. In this way, the users of the system may know at which location along the vessel and/or guidewire the atherectomy device is currently positioned. As the atherectomy device is moved to a position along the vessel corresponding to a location along the path 640, the atherectomy device may automatically implement the recommended settings (e.g., the settings 922, 924, and/or 926) associated with the locations along the guidewire 640. As an example, a location 1040 along the guidewire may be associated with a location 1030 along the pathway 640. The location 1030 may be the most proximal location of the region 850. It may be the first location along the vessel encountered by the atherectomy device 1020 during a treatment procedure with an obstruction requiring treatment. In this scenario, as the user of the system moves the atherectomy device to the location 1040, based on the recommendation settings associated with the location 1030, the atherectomy device may be engaged to an "On" status. In addition, the atherectomy device may adjust the fluence and pulse rate settings according to the recommended data. For example, a recommended fluence setting for the location 1040 may be 75 mJ/mm² and a recommend pulse rate for the location 1040 may be 70 pulses/sec. As the atherectomy device 1020 is positioned at the location 1040 of the guidewire, the device may adjust the fluence setting to 75 mJ/mm² and the pulse rate to 70 pulses/sec.

As the atherectomy device 1020 continues to move in a distal direction from the location 1040, the device 1020 may continuously update its status and settings according to the recommendations of all the locations along the pathway 640.

In some embodiments, a user of the system 100 may adjust the recommended settings of the atherectomy device 1020 during a treatment procedure. For example, if a user of the system observes that the recommended settings corresponding to locations along the pathway 640 are generally higher than they should be at most or all locations along the vessel, the user may provide an input to the system 100 which reduces the recommended fluence setting at all locations along the pathway 640 or reduces the recommended pulse rate setting at all locations along the pathway 640 or both. Similarly, if a user observes that the recommended settings corresponding to locations along the pathway 640 are generally lower than they should be, the user may provide a similar input generally increasing either the fluence setting or the rate setting or both.

Figure 11:
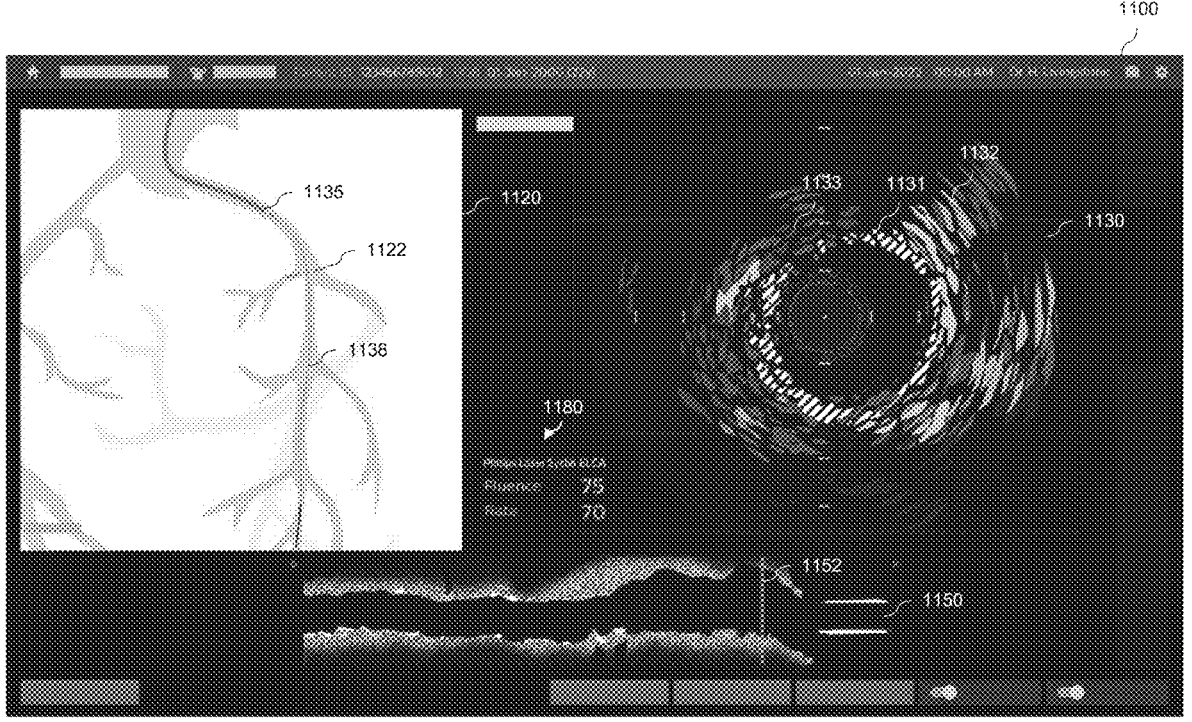
FIG. 11 is a diagrammatic view of an exemplary graphical user interface corresponding to an atherectomy procedure including an extraluminal image, an intravascular ultrasound image, and a longitudinal view of the vessel, according to aspects of the present disclosure.

FIG. 11 is a diagrammatic view of an exemplary graphical user interface 1100 corresponding to an atherectomy procedure including an extraluminal image 1120, an intravascular ultrasound image 1130, and a longitudinal view 1150 of the vessel, according to aspects of the present disclosure.

The IVUS image 1130 shown in FIG. 11 may be any of the received IVUS images during an IVUS imaging pullback procedure. Similar to the image 700 described with reference to FIG. 7, the IVUS image 1130 may include an indication of various different tissues or materials within the image 1130, such as calcium 1131, an additional tissue or material 1132 and 1133. The IVUS image 1130 may also include a depiction of a vessel wall, a lumen boundary, a stent wall, or any other feature. In some embodiments, the IVUS image 1130 may additionally display various graphical elements used to identify or highlight features of the image 1130. For example, any suitable graphical elements may be overlaid over the image 1130 to identify different tissues or materials, or a vessel wall, a lumen boundary, a stent wall, or any other features.

The graphical user interface 1100 may additionally display various metrics 1180. For example, the metrics 1180 may be associated with the displayed IVUS image 1130. The metrics 1180 may include recommended statuses or settings of the atherectomy device associated with the IVUS image 1130 shown. For example, the metrics 1180 may include an atherectomy device status of "On." As shown in FIG. 11, the metrics 1180 may also include recommended atherectomy device settings for fluence and pulse rate of 75 mJ/mm² and 70 pulses/sec respectively. In some aspects, the metrics 1180 may include measured cross-sectional areas of any of the tissues and/or materials related to an obstruction detected in the IVUS image 1130. In some embodiments, the metrics 1180 may include a label of the IVUS image 1130. The label may include a number referring to the order at which the IVUS image 1130 was acquired in comparison to other IVUS images. The title may also include an indication of any point of interest associated with the IVUS image 1130, including, for example, that the image corresponds to a minimum stent area, a maximum stent area, a minimum lumen area, a maximum lumen area, a minimum vessel area, a maximum vessel area, a minimum stent expansion, a maximum stent expansion, a minimum plaque burden, a maximum plaque burden, or any other features of interest associated with the image 1130. In some embodiments, the metric 1180 may include a stent area metric, a lumen area metric, a vessel area metric, a plaque burden, and an expansion metric, as well as any other metrics.

The extraluminal image 1120 may be any of the extraluminal images described with reference to FIG. 10. In some embodiments, the extraluminal image 1120 may be a no-contrast x-ray image. A depiction of a guidewire 1138 may also be present in the extraluminal image 1120 in some embodiments. The extraluminal image 1120 may also include an indicator 1122. This indicator 1122 may be overlaid over a portion of the guidewire 138 or a portion of the vessel imaged or treated. The indicator 1122 may illustrate, for a user, the location at which the IVUS image 1130 displayed proximate to the image 1120 was acquired.

Additionally included in the extraluminal image 1120 may be a depiction of the atherectomy device 1135. As has been explained, the extraluminal image 1120 may be continually updated during a live atherectomy procedure. In such an example, the user of the system 100 may see the atherectomy device 1135 moving through the patient anatomy along the guidewire 1138 and/or within the vessel and know where within the patient anatomy the atherectomy device is located. As each image 1120 is continuously updated, the position of the atherectomy device 1135 may move according to the direction of the user of the system.

Various aspects of displaying data and measurements from a planning/imaging phase of a procedure during a treatment phase of the procedure for guidance may include one or more features described in U.S. Provisional Application No. 63/187,961, filed May 13, 2021, and titled "INTRALUMINAL TREATMENT GUIDANCE FROM PRIOR EXTRALUMINAL IMAGING, INTRALUMINAL DATA, AND COREGISTRATION" and/or U.S. Provisional Application No. 63/090,638, filed Oct. 12, 2020, and titled "EXTRALUMINAL IMAGING BASED INTRALUMINAL THERAPY GUIDANCE SYSTEMS, DEVICES, AND METHODS", each of which are herein incorporated by reference in its entirety.

The graphical user interface 1100 may also include one example of a longitudinal intraluminal image 1150. The longitudinal image 1150 may be referred to as in-line digital (ILD) display or intravascular longitudinal display (ILD) 1150. The IVUS images acquired during an intravascular ultrasound imaging procedure, such as during an IVUS pullback, may be used to create the ILD 1150. In that regard, an IVUS image is a tomographic or radial cross-sectional view of the blood vessel. The ILD 1150 provides a longitudinal cross-sectional view of the blood vessel. The ILD 1150 can be a stack of the IVUS images acquired at various positions along the vessel, such that the longitudinal view of the ILD 1150 is perpendicular to the radial cross-sectional view of the IVUS images. In such an embodiment, the ILD 1150 may show the length of the vessel, whereas an individual IVUS image is a single radial cross-sectional image at a given location along the length. In another embodiment, the ILD 1150 may be a stack of the IVUS images acquired overtime during the imaging procedure and the length of the ILD 1150 may represent time or duration of the imaging procedure. The ILD 1150 may be generated and displayed in real time or near real time during the pullback procedure. As each additional IVUS image is acquired, it may be added to the ILD 1150. For example, at a point in time during the pullback procedure, the ILD 1150 shown in FIG. 11 may be partially complete. In some embodiments, the processor circuit may generate an illustration of a longitudinal view of the vessel being imaged based on the received IVUS images. For example, rather than displaying actual vessel image data, the illustration may be a stylized version of the vessel, with e.g., continuous lines showing the lumen border and vessel border.

An indicator 1152 may be displayed overlaid over the ILD 1150. This indicator 1152 may identify the location at which the IVUS image 1130 was obtained. In this way, the indicator 1152 may be similar to the indicator 1122 of the extraluminal image 1120. In some embodiments, the processor circuit 510 may be configured to receive an input from a user moving either the indicator 1122 or the indicator 1152. As either is selected and moved, the circuit 510 may be configured to move the unselected indicator to a corresponding location. In addition, the IVUS image corresponding to the new location may be displayed on the interface 1100 and accompanying metrics 1180 may be updated. In some embodiments, various regions of the ILD 1150 and/or extraluminal image 1120 may be identified or highlighted or otherwise differentiated by the processor circuit 510 corresponding to regions of interest, such as regions of increased obstructions such as the region 850 described with reference to FIG. 8.

Figure 12:
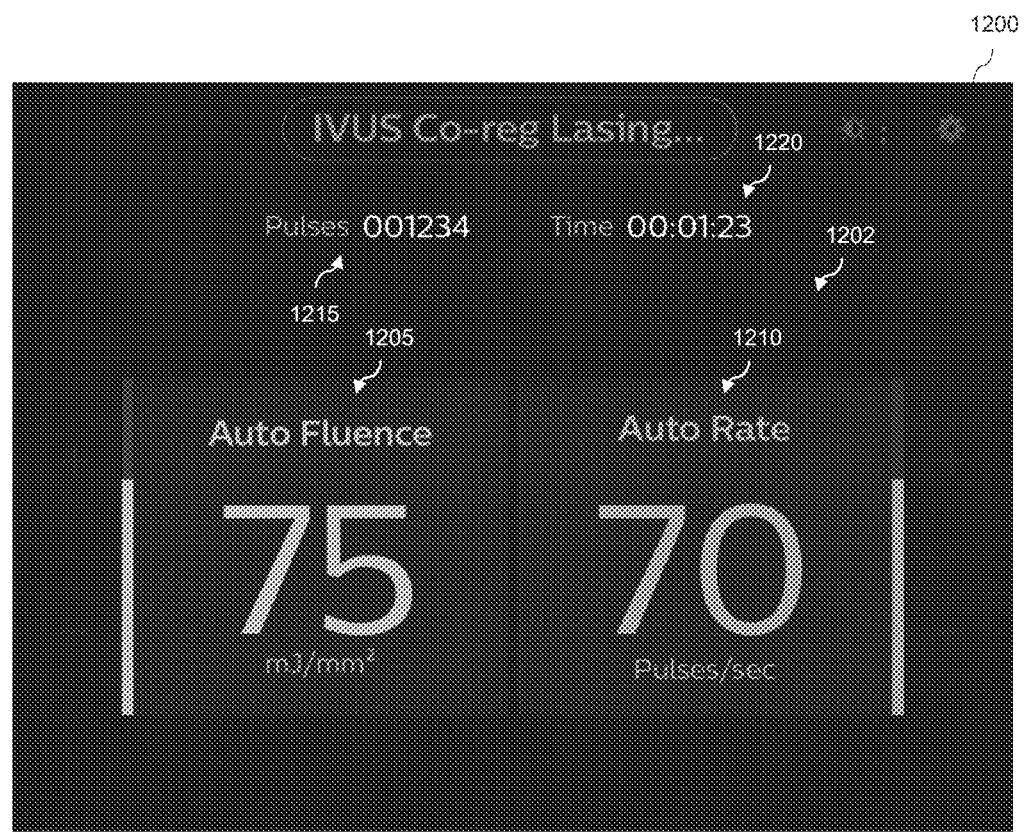
FIG. 12 is a diagrammatic view of a graphical user interface displaying atherectomy settings, according to aspects of the present disclosure.

FIG. 12 is a diagrammatic view of a graphical user interface 1200 displaying atherectomy settings 1202, according to aspects of the present disclosure. The graphical user interface 1200 includes an auto fluence metric 1205, an auto rate metric 1210, a pulse metric 1215, and a time metric 1220.

In some embodiments, the graphical user interface 1200 may be incorporated as a part of the graphical user interface 1100. For example, the graphical user interface 1200 may be overlaid at any suitable location within the graphical user interface 1100. In some embodiments, the graphical user interface 1200 may be displayed to a user on a separate display from the display used to show the graphical user interface 1100. In some embodiments, the same display (e.g., the display 132) may simultaneously display the interface 1100 and the interface 1200. In some embodiments, a user may select to view either the display 1100 or the display 1200 by a user input.

The auto fluence metric 1205 and auto rate metric 1210 may be displayed to a user of the system during an atherectomy procedure. In some embodiments, the auto fluence metric 1205 shown in FIG. 12 may correspond to a recommended fluence setting of the atherectomy device at the current location of the atherectomy device. Similarly, the auto rate metric 1210 may correspond to a recommended pulse rate setting of the atherectomy device at the current location of the atherectomy device. In other embodiments, the auto fluence setting 1205 and auto rate setting 1210 may refer to respective recommended settings at the location of a selected IVUS image, such as the location shown by the indicator 1152 and/or 1122 of FIG. 11. In some embodiments, a user of the system may select whether the auto fluence metric 1205 and the auto rate metric 1210 correspond to a current position of the atherectomy device or a selected location by a user input.

The pulse metric 1215 shown in graphical user interface 1200 may indicate to a user the number of pulses emitted by the atherectomy device 135 during a given procedure. The time metric 1220 may indicate an elapsed time of a given procedure. This time metric 1220 may measure the time which has passed from the time the atherectomy device was placed within the patient, the time extraluminal images began to be received, the time an intravascular imaging device was placed within a patient, or any other time.

FIG. 13 is a flow diagram of a method 1300 of automatically adjusting laser atherectomy settings based on coregistration of intraluminal data and extraluminal data, according to aspects of the present disclosure. The method 1300 may describe an automatic segmentation of a vessel to detect segments of interest using co-registration of invasive physiology and x-ray images. As illustrated, the method 1300 includes a number of enumerated steps, but embodiments of the method 1300 may include additional steps before, after, or in between the enumerated steps. In some embodiments, one or more of the enumerated steps may be omitted, performed in a different order, or performed concurrently. The steps of the method 1300 can be carried out by any suitable component within the system 100 and all steps need not be carried out by the same component. In some embodiments, one or more steps of the method 1300 can be performed by, or at the direction of, a processor circuit of the diagnostic system 100, including, e.g., the processor 560 (FIG. 5) or any other component.

At step 1310, the method 1300 includes receiving an intraluminal image obtained by the intraluminal imaging device when the intraluminal imaging device is located at a position within a body lumen of a patient. In some aspects, the method 1300 may include receiving a first plurality of x-ray images obtained by the x-ray imaging device during movement of the intravascular imaging device within a blood vessel of a patient, wherein the first plurality of x-ray images show a radiopaque portion of the intravascular imaging device and receiving a plurality of intravascular images obtained by the intravascular imaging device during the movement of the intravascular imaging device.

At step 1320, the method 1300 includes determining a tissue classification for tissue depicted in the intraluminal image. In some aspects, the method 1300 includes determining a plurality of tissue classifications for the plurality of IVUS images At step 1330, the method 1300 includes determining a laser atherectomy setting for the position based on the tissue classification. In some aspects, the method 1300 includes determining a plurality of laser atherectomy settings based on the plurality of tissue classification. In that regard, the method 1300 may include associating the plurality of laser atherectomy settings with corresponding positions along the blood vessel.

At step 1340, the method 1300 includes automatically controlling, with the laser atherectomy setting, the laser atherectomy device to perform laser atherectomy when the laser atherectomy device is located at the position within the body lumen. In some aspects, the method 1300 may include automatically applying the laser atherectomy setting to the laser atherectomy device to perform laser atherectomy when the laser atherectomy device is located at the position within the body lumen. In some aspects, the method 1300 may alternatively include applying a therapeutic procedure device setting to any suitable invasive therapeutic device. In some aspects, during a laser atherectomy procedure, the method 1300 may include receiving a second plurality of x-ray images obtained by the x-ray imaging device during movement of the laser atherectomy device within the blood vessel. The second plurality of x-ray images may show a radiopaque portion of the laser atherectomy device. As the laser atherectomy device is positioned at each position of the corresponding positions, the method may include applying a laser atherectomy setting of the plurality of laser atherectomy settings associated with the position of the laser atherectomy device, outputting to a screen display in communication with processor circuit, a screen display comprising: an intravascular image of the plurality of intravascular images associated with the position of the laser atherectomy device; the laser atherectomy setting; and an x-ray image of the second plurality of x-ray images showing the radiopaque portion of the laser atherectomy device.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system comprising:
one or more processors configured for communication with an intravascular imaging catheter and a laser atherectomy catheter distinct from the intravascular imaging catheter, wherein the one or more processors are configured to:
control, during an intravascular imaging procedure, the intravascular imaging catheter to obtain a plurality of intravascular images of a plurality of positions along a blood vessel of a patient;
determine a plurality of patient-specific tissue classifications at the plurality of positions based on the plurality of intravascular images;
determine, using the plurality of patient-specific tissue classifications, a plurality of patient-specific numerical values of at least one of a fluence setting or a rate setting for the plurality of positions;
store, in a memory in communication with the one or more processors, an association between:
the plurality of patient-specific numerical values of at least one of the fluence setting or the rate setting; and
the plurality of positions;
determine, during a laser atherectomy procedure, that the laser atherectomy catheter is at a position of the plurality of positions, wherein the intravascular imaging procedure was previously completed prior to the laser atherectomy procedure;
automatically determine a patient-specific numerical value of at least one of the fluence setting or the rate setting for the determined position by retrieving the patient-specific numerical value of at least one of the fluence setting or the rate setting from the memory based solely on the determined position;

control the laser atherectomy catheter to perform the laser atherectomy procedure using the patient-specific numerical value of at least one of the fluence setting or the rate setting for the determined position; and output, to a display in communication with the one or more processors, a screen display during the laser atherectomy procedure, wherein the screen display comprises:

the patient-specific numerical value of at least one of the fluence setting or the rate setting for the determined position; and a label for the patient-specific numerical value of at least one of the fluence setting or the rate setting, wherein the label is configured to indicate that the patient-specific numerical value of at least one of the fluence setting or the rate setting was automatically determined by retrieving the patient-specific numerical value at least one of the fluence setting or the rate setting from the memory based solely on the determined position.

2. The system of claim 1, wherein, to determine the plurality of patient-specific tissue classifications, the one or more processors are configured to identify a region depicted in one or more of the plurality of intravascular images, wherein the region comprises a type of tissue.

3. The system of claim 2, wherein the type of tissue comprises calcium.

4. The system of claim 1, wherein the screen display further comprises:

at least one of an intravascular image of the plurality of intravascular images, an extraluminal image depicting the blood vessel, or a longitudinal view of the blood vessel generated based on a plurality of intravascular images.

5. The system of claim 1, wherein, when the laser atherectomy device changes from the determined position to a further position of the plurality of positions, the one or more processors are configured to automatically change:

from the patient-specific numerical value for at least one of the fluence setting or the rate setting for the determined position to a further patient-specific numerical value for at least one of the fluence setting or the rate setting for the further position.

6. The system of claim 5, wherein the one or more processors is configured to:

determine, during the laser atherectomy procedure, that the laser atherectomy catheter is at the further position during movement of the laser atherectomy catheter through the blood vessel;

automatically determine the further patient-specific numerical value of at least one of the fluence setting or the rate setting for the further position by retrieving the further patient-specific numerical value of at least one of the fluence setting or the rate setting from the memory based solely on the further position;

control the laser atherectomy catheter to perform the laser atherectomy procedure using the further patient-specific numerical value of at least one of the fluence setting or the rate setting for the further position; and change the screen display to include the further patient-specific numerical value of at least one of the fluence setting or the rate setting.

7. The system of claim 1, wherein the one or more processors are configured to:

perform co-registration between the plurality of positions and the plurality of patient specific tissue classifications.

8. The system of claim 7, wherein the one or more processors are configured to perform co-registration between the plurality of positions and the plurality of patient-specific numerical values of at least one of the fluence setting or the rate setting.

9. The system of claim 1, wherein the one or more processors are configured to control the laser atherectomy catheter using the patient-specific numerical value of at least one of the fluence setting or the rate setting automatically in response to the determination of the position of the laser atherectomy catheter.

10. The system of claim 1, wherein the one or more processors are configured to retrieve the patient-specific numerical value of at least one of the fluence setting or the rate setting from the memory automatically in response to the determination of the position of the laser atherectomy catheter.

11. The system of claim 1, wherein the screen display further comprises:

a quantity of pulses emitted by the laser atherectomy catheter during the laser atherectomy procedure; and an elapsed time of the laser atherectomy procedure.

12. A method comprising:

controlling an intravascular imaging catheter during an intravascular imaging procedure to obtain a plurality of intravascular images of a plurality of positions along a blood vessel of a patient;

determining a plurality of patient-specific tissue classifications at the plurality of positions based on the plurality of intravascular images;

determining, using the plurality of patient-specific tissue classifications, a plurality of patient-specific numerical values of at least one of a fluence setting or a rate setting for the plurality of positions;

storing, in a memory, an association between:

the plurality of patient-specific numerical values of at least one of the fluence setting or the rate setting; and the plurality of positions;

determining, during a laser atherectomy procedure, that a laser atherectomy catheter is at a position of the plurality of positions, wherein the intravascular imaging procedure was previously completed prior to the laser atherectomy procedure, wherein the laser atherectomy catheter is distinct from the intravascular imaging catheter;

automatically determining a patient-specific numerical value of at least one of the fluence setting or the rate setting for the determined position by retrieving the patient-specific numerical value of at least one of the fluence setting or the rate setting from the memory based solely on the determined position;

controlling the laser atherectomy catheter to perform the laser atherectomy procedure using the patient-specific numerical value of at least one of the fluence setting or the rate setting for the determined position; and outputting, to a display, a screen display during the laser atherectomy procedure, wherein the screen display comprises:

the patient-specific numerical value of at least one of the fluence setting or the rate setting for the determined position; and a label for the patient-specific numerical value of at least one of the fluence setting or the rate setting, wherein the label indicates that the patient-specific numerical value of at least one of the fluence setting or the rate setting was automatically determined by retrieving the patient-specific numerical value at least one of the fluence setting or the rate setting from the memory based solely on the determined position.

* * * * *